United States Patent [19]

Venuti

[11] Patent Number: 4,670,434
[45] Date of Patent: Jun. 2, 1987

[54] (2-OXO-3-METHYLENE-1,2,3,5-TETRAHYDROIMIDAZO[2,1-B]QUINAZOLINYL)OXYALKYLAMIDES USEFUL AS CYCLIC AMP PHOSPHODIESTERASE INHIBITORS

[75] Inventor: Michael C. Venuti, San Francisco, Calif.

[73] Assignee: Syntex (U.S.A.) Inc., Palo Alto, Calif.

[21] Appl. No.: 798,208

[22] Filed: Nov. 14, 1985

[51] Int. Cl.[4] .................. A61K 31/505; C07D 487/04
[52] U.S. Cl. .............................. 514/234; 260/544 N; 514/267; 544/115; 544/250; 544/165; 544/387; 546/146; 546/164; 546/166; 546/226; 548/491; 548/540; 560/23; 562/434; 564/142; 564/166
[58] Field of Search ................ 544/250, 115; 514/267, 514/234, 236

[56] References Cited

U.S. PATENT DOCUMENTS

| | | |
|---|---|---|
| Re. 31,617 | 6/1984 | Beverung, Jr. et al. ............ 544/250 |
| 3,932,407 | 1/1976 | Beverung, Jr. et al. ............ 544/250 |
| 4,070,470 | 1/1978 | Nakagawa et al. ............ 546/158 X |
| 4,313,947 | 2/1982 | Nakagawa et al. ................ 514/418 |
| 4,490,371 | 12/1984 | Jones et al. ......................... 514/234 |
| 4,596,806 | 6/1986 | Ishikawa et al. .................... 514/267 |

FOREIGN PATENT DOCUMENTS

| | | |
|---|---|---|
| 0000718 | 2/1979 | European Pat. Off. . |
| 0116948 | 8/1984 | European Pat. Off. ............ 544/250 |
| 2393795 | 1/1979 | France . |
| 54-163825 | 12/1979 | Japan . |
| 2001638 | 2/1979 | United Kingdom . |

OTHER PUBLICATIONS

*European Journal of Medicinal Chemistry*, 1982-17, No. 6d, pp. 547-556 by Keinzle et al.
*Journal of Pharmacology and Experimental Therapeutics*, vol. 211, No. (1979), pp. 26-30 by Hidaka et al.

Primary Examiner—Donald G. Daus
Assistant Examiner—Diana G. Rivers
Attorney, Agent, or Firm—Liza K. Toth; Tom M. Moran

[57] ABSTRACT

This invention relates to compounds of the formula

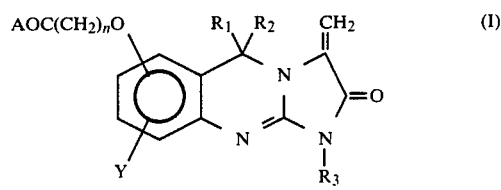

and the pharmaceutically acceptable acid addition salts thereof wherein the various substituents are defined herein. These compounds are cyclic AMP phosphodiesterase inhibitors useful as antithrombotic and inotropic agents in mammals.

10 Claims, No Drawings

(2-OXO-3-METHYLENE-1,2,3,5-TETRAHYDROIMIDAZO[2,1-B]QUINAZOLINYL)OXYALKYLAMIDES USEFUL AS CYCLIC AMP PHOSPHODIESTERASE INHIBITORS

BACKGROUND OF THE INVENTION

1. Field of the Invention

This invention relates to novel substituted 3-methylene-1,2,3,5-tetrahydroimidazo[2,1-b]quinazolines which possess phosphodiesterase inhibiting properties, and inotropic activities. More specifically the compounds of interest are (2-oxo-3-methylene-1,2,3,5-tetrahydroimidazo[2,1-b]quinazolinyl)oxyalkylamides and their pharmaceutically acceptable acid addition salts.

2. Related Art

Publications of possible interest herein are: F. Kienzle, et al, *Eur. J. Med.*, 1982-17, No. 6d, pp. 547–556, disclosing 1,5-dihydroimidazoquinazolinones as blood platelet aggregation inhibitors; Japanese Pat. No. 54-163825; and U.S. Pat. No. 3,932,407. See also U.S. Pat. No. 4,490,371, and U.S. Pat. No. 4,551,459, (the latter corresponding to Ser. No. 599,858, filed on Apr. 13, 1984), assigned to the assignee of the present invention, which disclose longer-acting (2-oxo-1,2,3,5-tetrahydroimidazo[2,1-b]quinazolinyl)oxyalkylamides.

SUMMARY OF THE INVENTION

In a first aspect, this invention is a compound of the formula

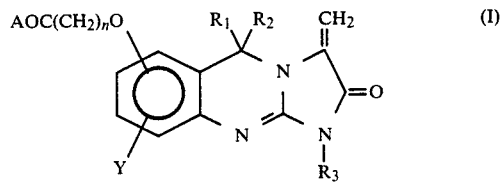

or an optical isomer thereof or a pharmaceutically acceptable acid addition salt thereof, wherein $n$ is 1 or an integer of 3 to 6;

$R_1$ is hydrogen or alkyl of 1 to 4 carbon atoms;

$R_2$ is hydrogen or $R_1$ and $R_2$ are combined to form an oxo group;

$R_3$ is hydrogen, alkyl of 1 to 6 carbon atoms, benzyl, or hydroxy lower alkyl;

Y is hydrogen, alkyl of 1 to 4 carbon atoms, halo or lower alkoxy;

A is either:

$NR_5R_6$ wherein $R_5$ an $R_6$ are independently selected from the group consisting of: hydrogen; alkyl of 1 to 6 carbon atoms; hydroxyalkyl of 1 to 6 carbon atoms or an aliphatic acylate thereof of 1 to 6 carbon atoms or an aryl acylate thereof of 7 to 12 carbon atoms; cycloalkyl of 3 to 8 carbon atoms or cycloalkyl lower alkyl of 4 to 12 carbon atoms wherein the cycloalkyl ring is unsubstituted or substituted with a lower alkyl, lower alkoxy, $-OCOR_7$, halo, $-NH_2$, $-N(R_7)_2$, $-NHCOR_7$, or $-COO(R_7)$ group wherein $R_7$ is lower alkyl; and phenyl or phenyl lower alkyl wherein in either case the phenyl ring is unsubstituted or substituted with at least one lower alkyl, halo or lower alkoxy group or an $-N(R_7)_2$, $-NHCOR_7$, or $-COOR_7$ group wherein $R_7$ is lower alkyl; or a radical selected from the group consisting of: morpholinyl; piperidinyl; perhexylenyl; N-loweralkylpiperazinyl; pyrrolidinyl; tetrahydroquinolinyl; tetrahydroisoquinolinyl; (±)-decahydroquinolinyl; and indolinyl.

In a second aspect, this invention is a pharmaceutically acceptable composition of one or more compounds according to Formula I wherein said compounds are combined with at least one pharmaceutically acceptable excipient.

In another aspect, this invention is a method for inhibiting 3',5'-cyclic AMP phosphodiesterase activity in a mammal, particularly, a human.

In yet another aspect, this invention is a method of treating heart failure by stimulating suppressed heart activity which occurs during heart failure.

The above three methods comprise administering a therapeutically effective amount of a compound of this invention alone or in admixture with a pharmaceutically acceptable excipient.

In yet another aspect, this invention is a process for making a compound of Formula I which method is related in the following detailed description.

DETAILED DESCRIPTION OF THE INVENTION

Utility

The compounds of this invention are potent inhibitors of platelet cyclic AMP phosphodiesterase activity in mammals. As a consequence, these compounds inhibit the ADP-induced aggregation of human platelets. Thus, these compounds are useful in the prevention or treatment of a variety of conditions related to platelet aggregation and thrombosis. Such conditions include intravascular thrombosis, coronary thrombosis, transient ischemic episodes, thrombosis, platelet thrombosis, thrombocytopenia, and platelet activation associated with the use of prosthetic devices (artificial heart valves, etc.).

Cyclic AMP is known to regulate the activity of numerous enzymes and mediates the action of several hormones. Studies have demonstrated that a deficiency in cyclic AMP or an increase in the activity of a high affinity cyclic AMP phosphodiesterase is associated with a variety of disease states. As inhibitors of 3',5'-cyclic AMP phosphodiesterase, compounds of this type are useful in the treatment or prevention of hypertension, asthma, diabetes, obesity, immune dysfunctions, psoriasis, inflammation, cardiovascular disease, tumor metastasis, cancer and hyperthyroidism. A full and more complete description of the various prophylactic and therapeutic activities of cyclic AMP phosphodiesterase inhibiting compounds can be found in the following several references: Amer, S. M., "Cyclic Nucleotides As Targets For Drug Design," *Advances in Drug Research*, Vol. 12, 1977, Academic Press, London, pp 1–38; Weinryh, I. et al, *J. Pharm. Sci.*, pp 1556–1567, (1972); Amer, S. M. & W. E. Kreighbaum, *J. Pharm. Sci.*, V 64, pp 1–37, (1975); and Harris, D. N., et al, *Enzyme Inhibitors As Drugs*, McMillan & Co., Ed-M. Sandler, pp 127–146, (1980).

The compounds of the present invention also have inotropic activity. They can strengthen myocardial contraction force by which the heart ventricles can pump the blood into the periphery. Consequently, these compounds also are useful in treating myocardial failure.

The compounds of this invention are particularly advantageous as inotropic agents because of their potent but short duration of action when administered intravenously. These properties are particularly valuable in cases where the compound is being administered intravenously and where it is important to accurately control the dosage level.

Definitions

The compounds of the present invention are numbered as follows:

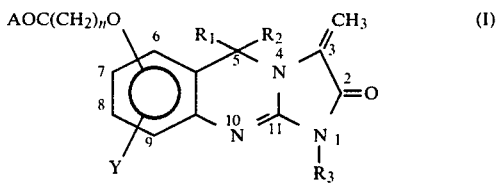

For the purpose of this disclosure, the compounds of the present invention are represented as having the single structural formulation represented by Formula I. However, when $R_3$ is hydrogen, compounds of Formula I can exist in several possible tautomeric forms established by the following core structures:

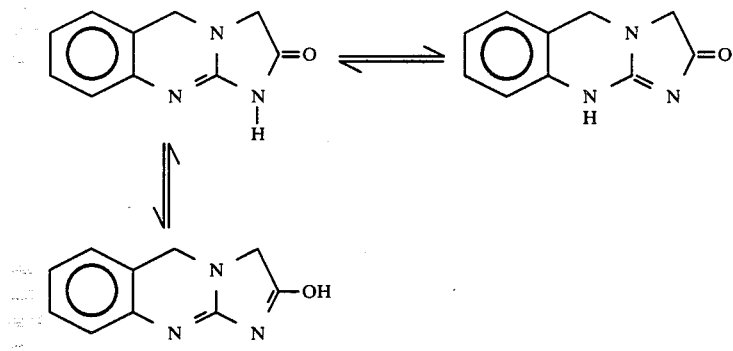

All tautomers are part of the present invention.

The compounds of this invention may be prepared as structural isomers wherein the oxyalkylamide side chain is substituted on the benzene ring at any of the four different available positions. This fact is graphically represented in the generic formula by the drawing of the line into the benzene ring without it being directed to a particular carbon. In addition, the Y substituent may be present at any of the remaining ring positions as indicated by Formula I.

Also within the scope of this invention are the optical isomers of those compounds having an asymmetric center, such as when position 5 of the 1,2,3,5-tetrahydroimidazo[2,1-b]quinazolin-2-one structure is substituted with a substituent other than hydrogen. When A is a substituent which has optical activity, such as when A is a cyclic compound, for example, (+)- or (−)-decahydroquinolinyl, then the instant compounds also will have optical activity.

Accordingly, the compounds of the present invention may be prepared either in optically active form or as racemic mixtures. Unless otherwise specified, where appropriate, products of the various synthetic steps described herein will be a racemic mixture. However, the scope of the subject invention herein is not limited to the racemic mixture, but is to encompass the separated individual optical isomers of the disclosed compounds.

If desired, the compounds herein may be resolved into their optical antipodes by conventional resolution means, for example, by separation (e.g. fractional crystallization) of the diastereomeric salts formed by the reaction of these compounds with optically active acids. Exemplary of such optically active acids are the optically active forms of camphor-10-sulfonic acid, 2-bromo-camphor-α-sulfonic acid, camphoric acid, menthoxyacetic acid, tartaric acid, malic acid, diacetyltartaric acid, pyrrolidine-5-carboxylic acid and the like. The separated pure diastereomeric salts may then be cleaved by standard means to afford the respective optical isomers.

For the purpose of this invention, the following phrases should be understood to have the recited meaning.

When reference is made to "alkyl of 2 to 6 carbon atoms" it is meant that there is a branched or unbranched saturated hydrocarbon chain containing, in total, that number of carbon atoms. The phrase refers specifically to such substituents as, for example, methyl, ethyl, n-propyl, i-propyl, n-butyl, tert-butyl, n-pentyl, n-hexyl and the like. The terms "alkyl of 1 to 4 carbon atoms" and "lower alkyl" are used interchangeably and mean methyl, ethyl, n-propyl, i-propyl, n-butyl, t-butyl and the like. When the term "alkyl" or prefix "alk" (such as in alkoxy) is used without qualification (such as the term "lower"), a branched or unbranched saturated hydrocarbon chain having from 1 to 12 carbon atoms is contemplated.

"Lower alkoxy" means the group —OR wherein R is lower alkyl as defined in the foregoing paragraph.

When it is recited that $R_1$ and $R_2$ can be combined to form an oxo group, it is meant that at position 5, as numbered above, the carbon has a double bond to an oxygen atom.

An "hydroxyalkyl" substituent is comprised of 2 to 6 carbon atoms, hydrogen and one oxygen atom, e.g., an alcohol wherein one terminal carbon atom is substituted on the amide nitrogen and the hydroxyl group is substituted on another carbon, preferably the ω-carbon. Herein the alkyl chain may be straight or branched, preferably straight, is fully saturated and, except for the hydroxyl group, has no other substitution. Examples of hydroxyalkyl substituents are 2-hydroxyethyl, 3-hydroxypropyl, 4-hydroxybutyl, 5-hydroxypentyl and 6-hydroxyhexyl. This is not an exhaustive list of hydroxyalkyl substituents that can be prepared by or used in this invention. It is merely intended to exemplify and identify that which is being referred to by the aforementioned phrase.

In the instance where the nitrogen in the amide-forming group and/or $R_3$ is substituted with an hydroxyalkyl substituent, the hydroxy function(s) can be converted to an ester by reaction with a carboxylic acid. Such an acid may be any unbranched or branched aliphatic acid having 1 to 6 carbon atoms such as, for example, formic acid, acetic acid, propionic acid, butyric acid, pentanoic acid, hexanoic acid or an isomer of these acids which has up to 6 carbons atoms and is fully saturated. These esters are referred to herein as "aliphatic acylates of 1 to 6 carbon atoms." In addition, the carboxylic acid may be an aryl acid, exemplified by benzoic acid and having up to 7 to 12 carbon atoms. Representative compounds are, in addition to benzoic acid, phenylacetic acid, 3-phenylpropionic acid, 4-phenylbutyric acid, 6-phenylhexanoic acid and the like. Such acids serve to define and exemplify the term, directed to the ester product of the reaction, "aryl acylates of 7 to 12 carbon atoms."

The term, "α-amino acid side chains," is meant to include amino acid side chains on naturally occurring amino acids and on commercially available synthetic amino acids, and amino acid side chains which can be synthesized or otherwise obtained by one of ordinary skill in the art of organic chemistry; where in each instance the amino group and the side chain are both attached to the α-carbon. Examples include amino acid side chains such as those found on cysteine, tyrosine, histidine, arginine, proline, phenylalanine, methionine, etc.

The phrase "unsubstituted or substituted" is used herein in conjunction with cycloalkyl and aryl substituents to indicate the ring may have on it only hydrogen or, alternatively, may be substituted with one or more of the enumerated radicals as specifically indicated.

"Cycloalkyl of 3 to 8 carbon atoms" refers to a saturated aliphatic ring which contains 3 to 8 carbon atoms and which is substituted directly onto the nitrogen without any intervening methylene groups. Such radicals are, for example, cyclopropyl, cyclobutyl, cyclopentyl, cyclohexyl, cycloheptyl and cyclooctyl.

When reference is made to "cycloalkyl lower alkyl of 4 to 12 carbon atoms," it is meant that the substituents denoted as cycloalkyl of 3 to 8 carbon atoms in the preceding paragraph are attached to the nitrogen of the amide-forming group (i.e., the group designated "A") by means of a saturated branched or unbranched carbon chain which may have 1 to 4 carbon atoms. Such substituents are, for example, cyclobutylmethyl, 4-cyclobutylbutyl, cyclopentylmethyl, 4-cyclopentylbutyl, cyclohexylmethyl, 4-cyclohexylbutyl, cycloheptylmethyl and 4-cycloheptylbutyl, to name a few examples.

In addition, the cycloalkyl or cycloalkyl lower alkyl radicals recited in the two foregoing paragraphs may be substituted with a radical chosen from the group consisting of lower alkyl, lower alkoxy, —OCOR$_7$, halo, —N(R$_7$)$_2$, —NHCOR$_7$, and —COO(R$_7$) wherein R$_7$ is lower alkyl.

"Phenyl lower alkyl" means a group having at least one and up to four methylene groups with an ω-phenyl group. In this instance the carbon chain is linear, not branched. The phenyl group may be unsubstituted, i.e., contain only hydrogen, or it may be substituted with up to 5 substituents of a single functionality or a combination of the several recited substituents. Examples of unsubstituted phenyl lower alkyl are benzyl, phenylethyl, phenylpropyl and phenylbutyl. Examples of substituted phenyl lower alkyl are 4-halophenylalkyl, 2,4-dihalophenylalkyl, 2,4,6-trihalophenylalkyl or 2,3,4,5,6-pentahalo-phenylalkyl wherein halo is as defined below. In addition, the phenyl group may be substituted with one or more lower alkyl groups such as methyl, ethyl, propyl or the like. One or more lower alkoxy groups may also be substituted on the phenyl ring. In addition, the phenyl ring may be substituted with a radical chosen from the group consisting of —N(R$_7$)$_2$, —NHCOR$_7$, and —COOR$_7$ wherein R$_7$ is lower alkyl.

The term "halo" refers to fluoro, chloro and bromo and iodo.

The prefix D- and L- are used to describe the individual optical isomers having an asymmetric center at the 3 or 5 position in the 1,2,3,5-tetrahydroimidazo[2,1-b]quinazolin-2-one structure.

Perhexylenyl refers to the substituent dicyclohexyl-2-(2-piperidyl)ethane which is disclosed in British Pat. No. 1,025,578.

"Pharmaceutically acceptable acid addition salt" refers to a salt which retains the biological properties and efficacy of the free base and which is not biologically or otherwise undesirable, formed with an inorganic or organic acid. Inorganic acids which may be used are, for example, hydrochloric acid, hydrobromic acid, sulfuric acid, nitric acid, phosphoric acid and the like. Exemplary organic acids are acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

The compounds of Formula I in free base form may be converted to the acid addition salts by treating the base with a stoichiometric excess of the appropriate organic or inorganic acid. Typically, the free base is dissolved in a polar organic solvent such as ethanol or methanol, and the acid added thereto. The temperature is maintained between about 0° C. and about 100° C. The resulting acid addition salt precipitates spontaneously or may be brought out of solution with a less polar solvent.

Administration and Dosage

Administration of the active compound and salts thereof described herein can be via any of the accepted modes of administration for agents which are cyclic AMP phosphodiesterase inhibitors. These methods include oral, parenteral and otherwise systemic or aerosol forms.

The amount of active compound administered will of course, be dependent on the subject being treated, the type and severity of the affliction, the manner of administration, and the judgment of the prescribing physician. In any case, a therapeutically effective amount of the drug either alone or in combination with the various excipients listed above or otherwise known will be administered.

A "therapeutically effective amount," is that amount needed to effect the inhibition of platelet cyclic AMP phosphodiesterase and thus prevent or treat conditions related to platelet aggregation and thrombosis, or that amount needed to inhibit tumor growth. Generally, a therapeutically effective amount will be a total dose equivalent to approximately 0.1 about 5 mg of N-cyclohexyl-N-methyl-4-(2-oxo-3-methylene-1,2,3,5-tetrahydroimidazo-[2,1-b]quinazolin-7-yl)oxybutyramide per kg of body weight is meant, preferably administered intravenously. Of course, this range will vary depending upon the molecular weight of the specific compound of Formula I that is used, and the other considerations noted above.

Depending on the intended mode of administration, the compositions used may be in the form of solid, semisolid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula I or the pharmaceutically acceptable salts thereof and, in addition, may include other medicinal agents, pharmaceutical agents, carriers, adjuvants, etc.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain about 10%-95% active ingredient, preferably about 25-70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795 and 3,773,919.

For systemic administration via suppository, traditional binders and carriers include, e.g. polyalkylene glycols or triglycerides. Such suppositories may be formed from mixtures containing active ingredient in the range of about 0.5%-10%; preferably about 1 ∝ 2%.

Specifically Preferred Embodiments

Preferred embodiments of the present invention are those compounds wherein n is 3 or 4; $R_1$ and $R_2$ are hydrogen and $R_3$ is hydrogen or methyl; or compounds wherein n is 3 or 4, and $R_1$, $R_2$ and $R_3$ are hydrogen.

Most preferred embodiments are the aforementioned preferred classes, wherein the $R_5$ and $R_6$ substituents are independently selected from the group consisting of: alkyl of 1 to 6 carbon atoms; hydroxyalkyl of 2 to 6 carbon atoms or an aliphatic acylate thereof of 1 to 6 carbon atoms or an aryl acylate thereof of 7 to 12 carbon atoms; cycloalkyl of 3 to 8 carbon atoms; cycloalkyl lower alkyl of 4 to 12 carbon atoms; and phenyl or phenyl lower alkyl wherein the phenyl ring is unsubstituted or substituted with 1 or more lower alkyl, halo or lower alkoxy groups; or wherein the nitrogen, $R_5$ and $R_6$ together form a radical from the group consisting of perhexylenyl, (±)-decahydroquinolinyl, morpholinyl, piperidinyl, pyrrolindinyl, tetrahydroquinolinyl, tetrahydro- isoquinolinyl and indolinyl.

Most specifically preferred is the compound N-cyclohexyl-N-methyl-4-(2-oxo-3-methylene-1,2,3,5-tetrahydroimidazo-[2,1-b]quinazolin-7-yl)oxybutanamide.

PREPARATION AND EXAMPLES

Compounds of the present invention can be made by several methods. In this disclosure, the process for preparing the claimed compounds begins with a hydroxy-2-nitrobenzaldehyde which is reacted with an ω-haloalkylester which serves to introduce the alkyl side chain onto the benzene ring. The ester is then hydrolyzed, converted to the acid chloride and treated with the appropriate secondary amine to form the amide. If $R_1$ is to be a group other than hydrogen, that group is introduced into the compound at this point by treating the amide with an appropriate Grignard reagent, which reacts with the aldehyde function, and then oxidizing the resulting alcohol to the ketone. The aldehyde or ketone-containing amide is then treated with an α-amino acid or a salt thereof followed by a cyclization step employing a halo cyanogen and base. Acid addition salts, etc., are prepared from this base as needed or desired.

Compounds of the present invention are prepared by the reaction sequence outlined in the following Reaction Schemes.

REACTION SCHEME A

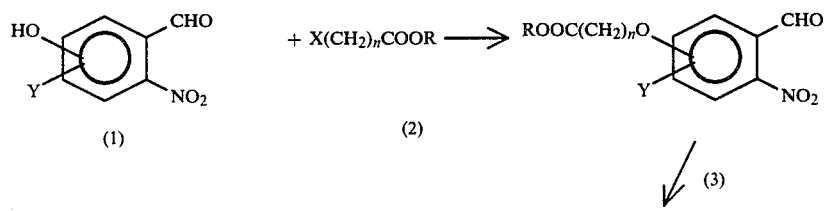

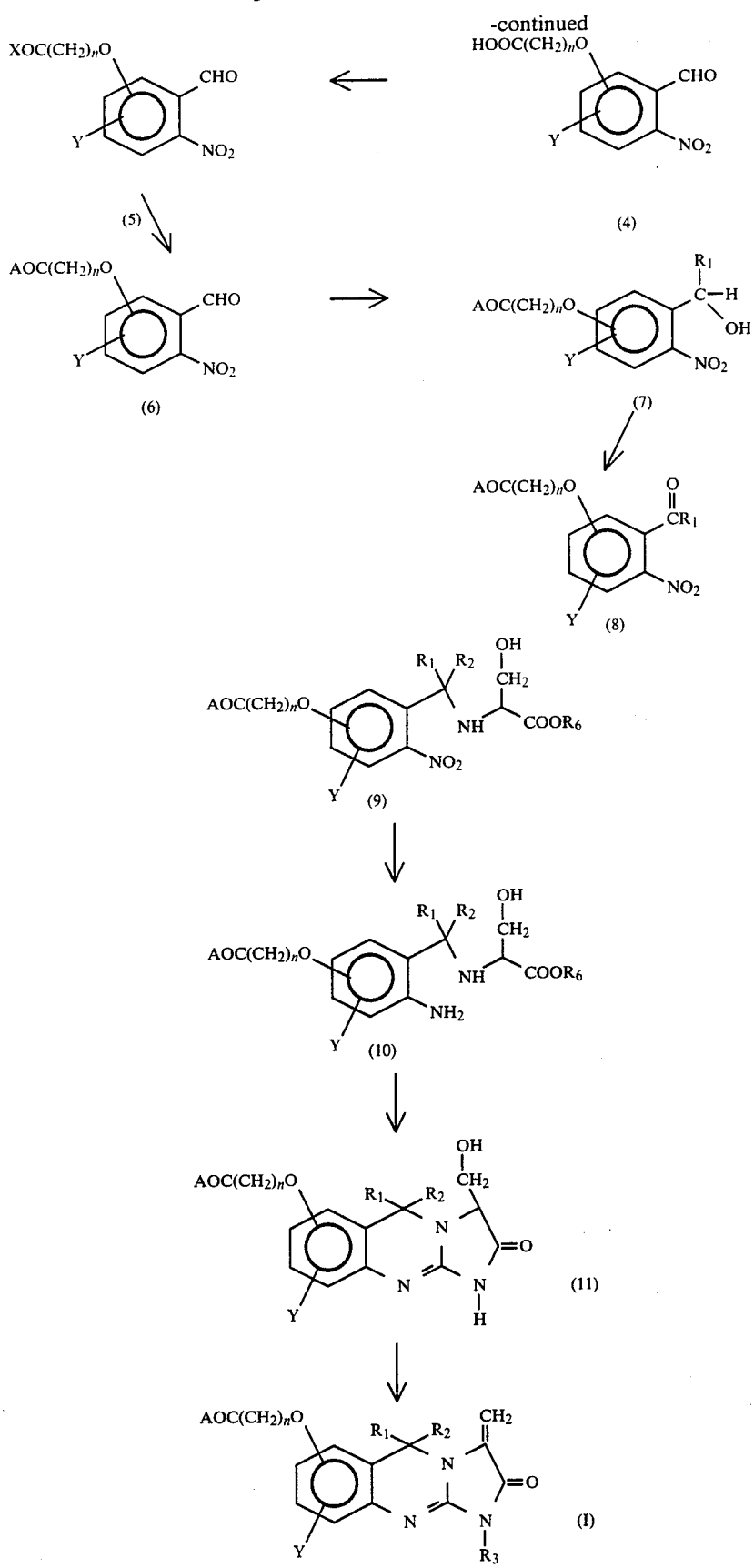
In Reaction Scheme A, the phenols of formula (1) are known in the art and a number of them are readily available from commercial sources such as Aldrich Chemical Co., Milwaukee, Wis. They are converted to the ω-(formylnitrophenyl)oxyalkyl esters by treating the phenol with an ω-halo substituted alkyl ester of formula (2). Generally, the reaction is carried out by mixing a mole equivalent of ω-haloalkylester, or up to a 20% excess thereof, with the parent phenol compound in a dry, dipolar aprotic solvent under an inert atmosphere. Solvents which may be used in this reaction are, for example dimethylformamide, propylene carbonate, ethylene carbonate, diethylcarbonate, dimethylcarbonate, tetrahydrofuran and the like. Dimethylformamide is preferred. Preferably the reaction will be carried out in a predried solvent and will be blanketed under a dry inert atmosphere such as nitrogen.

A molar amount, but up to a 30% excess, of weak base is added to the solution to effect the reaction. This weak base may be, for example, an alkali metal carbonate or the like, preferably potassium carbonate. The reaction requires between about 0.25 and about 2 hours at between about room temperature and about the boiling point of the solvent being used. Preferably the reaction will be carried out for about 1 hour at about 100° C.

Reaction products are isolated by conventional methodologies, preferably by solvent extraction into a compatible organic solvent. The formula (3) product may be further purified by distillation or other appropriate means.

Conversion of the ester to its corresponding acid involves saponification using well-known conditions and reagents. For example a dilute solution of a strong base such as an alkali metal base is added to an alcoholic solution of the ester in small portions and the reaction is allowed to run for about 10 to about 60 minutes at a temperature between about 0° and about 50° C. Alcohols which may be used as the solvent for this reaction are, for example, methanol, ethanol, propanol and isopropanol or the like, though it is preferable to use ethanol. The base may be, for example, sodium hydroxide, potassium hydroxide, or lithium hydroxide and the like, but it is preferable and most convenient to use sodium hydroxide. While the concentration of the added base may range between about 1 and about 6N it is preferable to begin with an approximately 3N solution and add it to the reaction mixture in a ratio of 1 part base for every 4 parts of alcohol solution. Preferably the reaction is allowed to run for about 30 minutes at room temperature after which the solution is neutralized with a concentrated solution of a strong acid such as hydrochloric acid or the like and the solvent evaporated. The product is then further isolated by organic solvent extraction. Crystallization from an appropriate organic solvent gives formula (4) type compounds.

The conversion of formula (4) acids to the acid chloride of formula (5) is a known reaction. The reaction is carried out in a stirred solution of acid in a non-polar, non-reactive solvent such as benzene or toluene or the like to which has been added a small amount of a dipolar aprotic solvent such as dimethylformamide or the like by the addition of an acid halide forming agent, preferably an acid chloride forming agent such as oxalyl chloride. The acid chloride forming reagent should be present in about a 25 to 75% molar excess, preferably about a 50% excess, in order to effect a stoichiometric conversion of the acid to the acid halide.

The reaction is allowed to proceed at a temperature between about 0° and about 45° C. for a time between about 15 minutes and about 2 hours. Preferable reaction conditions are about 20° C. for about 1 hour by which time the suspended acid should be completely dissolved.

Without further isolation, the solvent in which the acid chloride is dissolved is converted to a polar solvent by repetitive evaporation and dissolution of the acid chloride in the new polar solvent. This polar solvent may be, for example, an ether such as tetrahydrofuran or diethylether, preferably tetrahydrofuran and preferably dry.

Conversion of the acid chloride to the amide (formula 6) is carried out using Schotten-Baumann reaction conditions which involves dropwise addition of the acid chloride to a well-stirred, cooled mixture of a amine and a weak base in an aqueous organic solvent wherein the organic solvent is the same as that in which the acid chloride is dissolved. The amine should be present in a molar excess of about 30% while the weak base is preferably present in a molar excess of about 35%.

Weak bases having utility for this reaction are the alkali metal carbonates and the like, but particularly sodium carbonate. During addition of the acid chloride to the amine, the reaction mixture should be maintained at a temperature of about 0° C. When the addition of acid chloride is complete the cooling bath may be removed and the reaction allowed to proceed at between about 10°–45° C., but preferably at room temperature. The reaction is complete in about 15 minutes to about 2 hours, and most generally about 1 hour. Removal of the organic solvent leaves an aqueous solution which is extracted to obtain the amide. After appropriate washing of the organic layer, it is evaporated and the amide crystallized from an appropriate organic solvent or chromatographically purified before crystallization.

An alternative method for preparing amides is to catalyze their formation by means of 4-dimethylaminopyridine (DMAP) under anhydrous conditions and an inert atmosphere. The acid chloride, dissolved in a dipolar aprotic solvent, such as ethyl ether, is added to a solution of the amine which is dissolved in a dipolar aprotic solvent containing an additional base, for example a trialkylamine, or the like but preferably triethylamine. The amine will be present in a slight molar excess relative to the acid chloride. The DMAP catalyst is present in the mixture in an amount up to a 10% molar amount relative to the acid chloride. During addition of the acid chloride, the reaction mixture is maintained at a temperature of between $-10°$ to $+10°$ C. The inert atmosphere is preferably provided by the use of dry nitrogen.

When addition of the acid chloride is complete the solution is warmed to between about 15° and about 35° C., preferably room temperature, and the reaction is allowed to proceed at that temperature for between about 30 minutes and about 4 hours, preferably about 2 hours.

When the A group contains an hydroxyalkyl group, that group is acylated at this point in the synthesis. This protects the hydroxyl group from attack by mesylchloride and the like used in the later conversion of the 3-hydroxymethyl group to the 3-methylene group. This hydroxyalkyl group is acylated by treating the compound with the appropriate anhydride in pyridine under standard conditions.

When $R_1$ is alkyl or phenyl, that moiety may be introduced into the compound by reacting the formula (6) aldehyde with a Grignard reagent, an alkyl lithium compound, or an alkyl titanium complex, and then oxidizing the resulting secondary alcohol to the ketone represented by formula (8).

Alkyl magnesium halide reagents are readily available or may be easily prepared from the alkyl halide and magnesium, a process well-known in the synthetic arts. Formation of the alcohol is effected by adding the aldehyde to a cooled ethereal solution of Grignard reagent wherein the Grignard reagent is present in a 10% molar excess relative to the aldehyde. After addition of the aldehyde is complete, the reaction is refluxed for about 1 to 4 hours, preferably about 2 hours. Degradation of the magnesium halide derivative to obtain the alcohol is carried out by dropwise addition of a mineral acid, for example a 25% sulfuric acid solution. This solution is neutralized with a weak base and the alcohol isolated in preparation for treatment with an oxidizing agent to regenerate the carbonyl group.

More preferably, however, particularly when the aldehyde of formula (6) comprises the ester functionality required to protect the hydroxyalkyl side chain, an aldehyde of formula (6) is reacted with an alkyl or aryl titanium (IV) reagent, such as methyl triisopropoxy titanium. Such reagents, recently described by Seebach, et al., (in Modern Synthetic Methods, Vol. 3, Wiley, New York, N.Y., 1983,) offer distinct advantages in this particular reaction due to their high degree of selectivity for the aldehyde moiety, and their low propensity for side reactions. The procedure involves the addition of the aldehyde of formula (6) to a solution of the appropriate alkyl or aryl titanium (IV) reagent, generated in situ according to the reference cited. After the addition is complete, the mixture is evaporated, and the desired alcohol is obtained after aqueous workup.

The oxidation of formula (7) type compounds is carried out by means of a strong oxidizing agent under selected conditions which minimize amide oxidation. There may be used, for example, a chromium trioxide-pyridine complex or the like. Preferably the reaction will be carried out under anhydrous conditions under an inert atmosphere and in a polar organic solvent which is inert to the oxidizing reagent, such as a halogenated hydrocarbon. Reaction temperatures will between about 0° and about 100° C. for a period of about 1 to about 8 hours. A 10% molar excess of oxidizing agent relative to the alcohol is sufficient to effect the desired oxidation.

Herein a preferred oxidizing reagent is the Collins reagent [J. C. Collins, et al., *Tetrahedron Letters*, p 3363 (1968)] which employs a chromium trioxide-pyridine complex in a halogenated hydrocarbon solvent system. The reaction is carried out under anhydrous conditions in an inert atmosphere. The preferred organic solvents are for example, methylene chloride, carbon tetrachloride, ethylene chloride, or the like. The inert atmosphere is maintained by the use of a dry inert gas, preferably dry nitrogen. Usually a temperature between about 0° to about 50° C. for a period of about 0.5 to about 5 hours is generally sufficient to effect the reaction. Most preferably the reaction will be carried out in dry methylene chloride under a dry nitrogen atmosphere for about 1 hour at room temperature.

Formula (6) and formula (8) compounds are then converted to compounds of formula (9) by reacting the aldehyde or ketone with an ester of serine. Generally, the reaction is carried out at a temperature between about 0° and about 50° C., preferably ambient temperature. A time of between 1 to 8 hours is sufficient to effect the reaction though about 3 to 4 hours is preferable. The reaction is generally carried out in a polar solvent such as an alcohol, for example, methanol, ethanol, propanol, or the like in which the aldehyde/ketone and the ester are soluble. It is preferable to add a water-scavenging agent such as molecular sieves in order to remove water generated during the reaction process.

Initially, a reaction mixture is prepared which contains the carbonyl compound, about a two-fold molar amount of serine ester as an acid addition salt, and the water scavenging agent. To this mixture is added a large molar excess of the serine ester, about 6 to 10 fold excess. The solution is generally maintained between about 10° to about 30° C. during this addition process. After addition of the ester is complete, there is added a cyanoborohydride reducing agent in a molar amount of about one-half that of the carbonyl compound. The reaction is allowed to proceed at a temperature between about 10° to about 30° C., preferably at room temperature for a period of between about 1 to 6 hours, preferably about 3 to 4 hours.

While the reaction product (formula 9) may be isolated for characterization, etc., it is most convenient to simply remove precipitated solids, i.e, the molecular sieves and borate salts, by filtration, evaporate the solvent and to take up the residue in an organic solvent. This solution may then be washed with a base and brine to remove impurities after which the solvent is removed and the resulting residue used directly in the next reaction step.

Reduction of the nitro group is most conveniently carried out by catalytic hydrogenation. This reaction may be accomplished by conventionally known means. As practiced herein, the residue from the previous reaction step is dissolved in an appropriate solvent such as, for example, a simple alcohol such as methanol or ethanol. A transition metal catalyst which will selectively reduce the nitro group to the amine without affecting the amide or the phenyl ring is preferred. A preferred catalyst is a palladium catalyst and most preferably it will be palladium on carbon such as the readily available 10% palladium/carbon catalyst.

A small amount of the palladium/carbon catalyst, i.e., between 0.5 and 1.5 grams, will generally be sufficient to effect the reduction. The alcoholic reaction mixture is placed under hydrogen at room temperature and allowed to proceed till an equivalent of hydrogen has been taken up. Isolation of the hydrogenation product is readily accomplished by filtration to remove the catalyst after which the reaction product may be used directly in the following step.

Cyclization of the amine is achieved by means of a cyanogen halide, preferably the bromide. A 5 to 10% molar excess of cyanogen halide is added to the solution from the previous reaction. The resulting solution is refluxed overnight, preferably about 16 hours.

The resulting reaction mixture is then treated with a solution of a strong base for about 0.5 to about 4 hours at a temperature between about 0° and about 50° C. Bases which may be used to effect this reaction are preferably alkali metal bases such as sodium hydroxide, potassium hydroxide and the like. They are used at a concentration of between about 1 to about 6N, preferably about 2N. A molar amount of base equivalent to that of the cyanogen halide employed in the previous step is employed in this final reaction step. Preferably the reaction will be allowed to proceed for about 2 hours at room temperature during which time the product generally will precipitate as a powder. The product, formula 11, wherein $R_3$ is hydrogen, can be further isolated and characterized by filtration or centrifugation, followed by drying or by recrystallization from an appropriate organic solvent.

The dehydration of formula 11 to obtain the 3-methylene compounds of formula I is carried out essentially following conditions used in C. Shin, et al., *Bull. Chem. Soc. Jap.*, 54, 1132 (1981). In this instance, the reaction may be carried out in pyridine or a similar solvent using an hydroxy activating reagent such as mesylchloride or the like. The heterocycle is dissolved in the solvent to which is added about a 10 percent molar excess relative to the heterocycle. About 30 minutes later, a four-fold molar excess of N,N-diisopropylethylamine (DIPEA) or a similar amine, is added at between about 0° and about 5° C. This mixture is stirred for about 1 to 6 hours, preferably about 3 hours at about room temperature. The product is recovered by usual means.

If an N-hydroxyalkyl compound is wanted, the acylates prepared in the making of formula (6) are hydrolyzed in the same manner as described for the preparation of formula (4).

Further transformation of compounds of Formula I where $R_3$=H to those of Formula I where $R_3$ is alkyl, benzyl, etc is accomplished by treating the former with alkylating agents and a strong base, such as potassium tert-butoxide or sodium hydroxide in a dipolar aprotic solvent such as dimethyl formamide.

The compounds of formula I in free base form may be converted to the acid addition salts by treatment with a stoichiometric excess of the appropriate organic or inorganic acid. Typically, the free base is dissolved in a polar organic solvent such as ethanol or methanol, and the acid added thereto. The temperature is maintained between about 0° C. and 100° C. The resulting acid addition salt precipitates spontaneously or may be brought out of solution with a less polar solvent.

The acid addition salts of the compounds of Formula I may be decomposed to the corresponding free base by treatment with a stoichiometric excess of a suitable base, such as potassium carbonate or sodium hydroxide, typically in the presence of aqueous solvent, and at a temperature of between about 0° C. and 100° C. The free base form is isolated by conventional means, such as extraction with an organic solvent.

Salts of the compounds of Formula I may be interchanged by taking advantage of differential solubilities of the salts, volatilities or acidities of the acids, or by treating with the appropriately loaded ion exchange resin. For example, the interchange is effected by the reaction of a salt of the compounds of Formula I with a slight stoichiometric excess of an acid of a lower pKa than the acid component of the starting salt. This conversion is carried out at a temperature between about 0° C. and the boiling point of the solvent.

In summary, the preferred synthetic method generally comprises the steps of treating a compound of Formula II

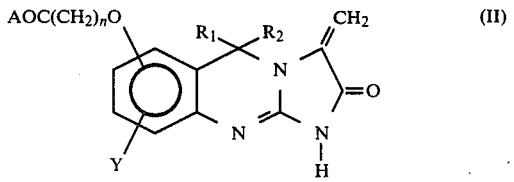

wherein
n, $R_1$, $R_2$, and Y are as defined above, with an N-alkylating agent, or treating a compound of Formula III which is

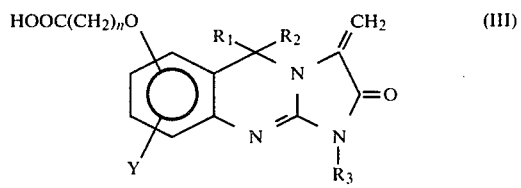

wherein
n, $R_1$, $R_2$, $R_3$ and Y are as defined above with an amide forming reagent; or
treating a compound of Formula IV

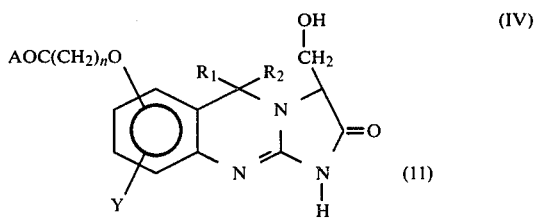

wherein
n, $R_1$, $R_2$, $R_3$, Y and A are as defined above, except that $R_5$ and $R_6$ of A are not hydroxyalkyl of 2 to 6 carbon atoms unless $R_5$ and $R_6$ have first been protected as aliphatic or aryl acylates, with mesylchloride or the like and diisopropylethylamine or the like;
converting the free base of a compound of formula I to a pharmaceutically acceptable acid addition salt; or
converting a salt of the compound of formula I to the corresponding free base; or
converting a salt of the compound of Formula I to a corresponding pharmaceutically acceptable acid addition salt.

The following Preparations and Examples are set forth to illustrate the reaction steps graphically recited above.

PREPARATION 1

Ethyl 4-(3-formyl-4-nitrophenyl)oxybutanoate and related compounds of Formula 3

The preparation of the compounds of Formula 3, ω-((formyl-nitrophenyl)oxy)-alkyl acid esters, is described herein.

To a solution of 5-hydroxy-2-nitrobenzaldehyde (84.0 g) and ethyl 4-bromobutanoate (86 ml) in dry dimethylformamide (500 ml) blanketed under dry nitrogen was added potassium carbonate (76.0 g). The reaction mixture was heated to 100° C. for 1 hour. This mixture was cooled, and the solvent removed by evaporation to give a drak brown syrup. This residue was partitioned between ethyl acetate and saturated sodium carbonate (500 ml each). The organic layer was washed with additional saturated sodium carbonate (3×500 ml), and with brine (2×500 ml), dried, filtered and evaporated to give a drak brown syrup. Kugelrohr distillation (180° C., 0.2 mm) afforded ethyl 4-((3-formyl-4-nitrophenyl)oxy)-butanoate (95 g) as a bright yellow syrup which slowly darkened upon standing.

Using the above procedure, but substituting the appropriate aldehyde for 5-hydroxy-2-nitrobenzaldehyde and alkyl ω-bromoalkylate for ethyl 4-bromobutanoate there are prepared, for example, the following compounds:

ethyl 4-(3-formyl-4-nitrophenyl)oxybutanoate;
ethyl 4-(3-nitro-4-formylphenyl)oxybutanoate;
ethyl 4-(2-formyl-3-nitrophenyl)oxybutanoate;
ethyl 4-(2-nitro-3-formylphenyl)oxybutanoate;
ethyl 4-(3-formyl-4-nitrophenyl)oxybutanoate;
ethyl 7-(3-formyl-4-nitrophenyl)oxyheptanoate;
ethyl 6-(3-formyl-4-nitrophenyl)oxyhexanoate;
ethyl 5-(3-formyl-4-nitrophenyl)oxypentanoate;
ethyl 4-(2-chloro-3-formyl-4-nitrophenyl)oxybutanoate;
ethyl 4-(3-formyl-4-nitro-5-chlorophenyl)oxybutanoate;
ethyl 4-(2-chloro-4-nitro-5-formylphenyl)oxybutanoate;
ethyl 4-(3-formyl-4-nitro-5-fluorophenyl)oxybutanoate;
ethyl 4-(2-fluoro-3-formyl-4-nitrophenyl)oxybutanoate;
ethyl 4-(2-methyl-3-formyl-4-nitrophenyl)oxybutanoate;
ethyl 4-(2-formyl-3-nitro-6-fluorophenyl)oxybutanoate;
ethyl 4-(2-formyl-3-nitro-4-chlorophenyl)oxybutanoate;
ethyl 4-(2-formyl-3-nitro-5-fluorophenyl)oxybutanoate;
ethyl 4-(2-formyl-3-nitrophenyl)oxybutanoate;
ethyl 4-(2-formyl-3-nitro-5-methylphenyl)oxybutanoate;
ethyl 4-(2-formyl-3-nitro-6-fluorophenyl)oxybutanoate;
ethyl 4-(2-nitro-3-formylphenyl)oxybutanoate;
ethyl 4-(2-nitro-3-formyl-5-methylphenyl)oxybutanoate;
ethyl 4-(3-nitro-4-formyl-6-fluorophenyl)oxybutanoate;
ethyl 4-(2-chloro-4-formyl-5-nitrophenyl)oxybutanoate;
ethyl 4-(3-nitro-4-formylphenyl)oxybutanoate;
ethyl 4-(3-nitro-4-formyl-5-methylphenyl)oxybutanoate;
ethyl 4-(2-nitro-3-formyl-6-fluorophenyl)oxybutanoate;
ethyl 4-(2-nitro-3-formyl-6-chlorophenyl)oxybutanoate;
ethyl 7-(3-formyl-4-nitrophenyl)oxyheptanoate;
ethyl 7-(2-chloro-3-formyl-4-nitrophenyl)heptanoate;
ethyl 7-(2-methyl-3-formyl-4-nitrophenyl)heptanoate;
ethyl 7-(3-formyl-4-nitro-5-chlorophenyl)heptanoate;
ethyl 7-(2-formyl-3-nitrophenyl)heptanoate;
ethyl 7-(2-formyl-3-nitro-4-fluorophenyl)heptanoate;
ethyl 7-(2-methyl-3-formyl-4-nitrophenyl)heptanoate;
ethyl 7-(2-formyl-3-nitro-5-chlorophenyl)heptanoate;
ethyl 7-(2-nitro-3-formylphenyl)heptanoate;
ethyl 7-(2-nitro-3-formyl-4-fluorophenyl)heptanoate;
ethyl 7-(2-nitro-3-formyl-6-chlorophenyl)heptanoate;
ethyl 7-(2-nitro-3-formyl-5-methylphenyl)heptanoate;
ethyl 7-(3-nitro-4-formylphenyl)heptanoate;
ethyl 7-(3-nitro-4-formyl-5-methylphenyl)heptanoate;
ethyl 5-(2-formyl-3-nitrophenyl)oxypentanoate;
ethyl 5-(2-formyl-3-nitro-4-chlorophenyl)oxypentanoate;
ethyl 5-(2-formyl-3-nitro-4-methylphenyl)oxypentanoate;
ethyl 5-(2-formyl-3-nitro-6-methylphenyl)oxypentanoate;
ethyl 5-(3-formyl-4-nitro-5-chlorophenyl)oxypentanoate;
ethyl 5-(2-chloro-3-formyl-4-nitrophenyl)oxypentanoate;
ethyl 5-(3-formyl-4-nitrophenyl)oxypentanoate;
ethyl 5-(3-nitro-4-formylphenyl)oxypentanoate;
ethyl 5-(3-nitro-4-formyl-5-methylphenyl)oxypentanoate;
ethyl 5-(3-nitro-4-formyl-6-chlorophenyl)oxypentanoate;
ethyl 5-(3-formyl-4-nitro-6-chlorophenyl)oxypentanoate;
ethyl 5-(2-nitro-3-formylphenyl)oxypentanoate;
ethyl 5-(2-nitro-3-formyl-4-methylphenyl)oxypentanoate;
ethyl 5-(2-nitro-3-formyl-6-chlorophenyl)oxypentanoate;
ethyl 6-(2-formyl-3-nitrophenyl)oxyhexanoate;
ethyl 6-(2-formyl-3-nitro-4-chlorophenyl)oxyhexanoate;
ethyl 6-(2-formyl-3-nitro-6-chlorophenyl)oxyhexanoate;
ethyl 6-(3-formyl-4-nitrophenyl)oxyhexanoate;
ethyl 6-(3-formyl-4-nitro-6-chlorophenyl)oxyhexanoate;
ethyl 6-(3-formyl-4-nitro-5-methylphenyl)oxyhexanoate;
ethyl 6-(2-nitro-3-formylphenyl)oxyhexanoate;
ethyl 6-(2-nitro-3-formyl-6-fluorophenyl)oxyhexanoate;
ethyl 6-(2-nitro-3-formyl-5-methylphenyl)oxyhexanoate;
ethyl 6-(3-nitro-4-formylphenyl)oxyhexanoate;
ethyl 6-(3-nitro-4-formyl-6-methylphenyl)oxyhexanoate;
ethyl 6-(3-nitro-4-formyl-5-chlorophenyl)oxyhexanoate;
ethyl 2-(2-chloro-3-formyl-4-nitrophenyl)oxyacetate;
ethyl 2-(3-formyl-4-nitrophenyl)oxyacetate;
ethyl 2-(3-formyl-4-nitro-5-chlorophenyl)oxyacetate;
ethyl 2-(2-chloro-4-nitro-5-formylphenyl)oxyacetate; and
ethyl 2-(3-formyl-4-nitro-5-fluorophenyl)oxyacetate.

PREPARATION 2

Ethyl 4-(3-formyl-4-nitrophenyl)oxybutanoic acid and related compounds of Formula 4

Ester hydrolysis to give the acids of formula 4 is described herein.

To a solution of ethyl 4-(3-formyl-4-nitrophenyl)oxybutanoate (65 g) in ethanol (400 ml) was added 3N NaOH (100 ml) in small portions. After 30 minutes at room temperature, the reaction mixture was acidified with concentrated HCl and the ethanol evaporated. The aqueous residue was extracted with ethyl acetate (4×200 ml). The combined organic layers were washed with brine (2×200 ml), dried over Na$_2$SO$_4$, filtered and evaporated to give a light yellow solid. Trituration with ether afforded 4-(3-formyl-4-nitrophenyl)oxybutanoic acid (55 g), m.p. 109°–110° C.

Following the above procedure, the esters prepared as per Preparation 1 are converted to the corresponding acid:

4-(3-formyl-4-nitrophenyl)oxybutanoic acid;
4-(3-nitro-4-formylphenyl)oxybutanoic acid;
4-(2-formyl-3-nitrophenyl)oxybutanoic acid;
4-(2-nitro-3-formylphenyl)oxybutanoic acid;
4-(3-formyl-4-nitrophenyl)oxybutanoic acid;
7-(3-formyl-4-nitrophenyl)oxyheptanoic acid;
6-(3-formyl-4-nitrophenyl)oxyhexanoic acid;
5-(3-formyl-4-nitophenyl)oxypentanoic acid;
4-(2-chloro-3-formyl-4-nitrophenyl)oxybutanoic acid;
4-(3-formyl-4-nitro-5-chlorophenyl)oxybutanoic acid;
4-(2-chloro-4-nitro-5-formylphenyl)oxybutanoic acid;
4-(3-formyl-4-nitro-5-fluorophenyl)oxybutanoic acid;
4-(2-fluoro-3-formyl-4-nitrophenyl)oxybutanoic acid;
4-(2-methyl-3-formyl-4-nitrophenyl)oxybutanoic acid;
4-(2-formyl-3-nitro-6-fluorophenyl)oxybutanoic acid;
4-(2-formyl-3-nitro-4-chlorophenyl)oxybutanoic acid;
4-(2-formyl-3-nitro-5-fluorophenyl)oxybutanoic acid;
4-(2-formyl-3-nitrophenyl)oxybutanoic acid;
4-(2-formyl-3-nitro-5-methylphenyl)oxybutanoic acid;
4-(2-formyl-3-nitro-6-fluorophenyl)oxybutanoic acid;
4-(2-nitro-3-formylphenyl)oxybutanoic acid;
4-(2-nitro-3-formyl-5-methylphenyl)oxybutanoic acid;
4-(3-nitro-4-formyl-6-fluorophenyl)oxybutanoic acid;
4-(2-chloro-4-formyl-5-nitrophenyl)oxybutanoic acid;
4-(3-nitro-4-formylphenyl)oxybutanoic acid;
4-(3-nitro-4-formyl-5-methylphenyl)oxybutanoic acid;
4-(2-nitro-3-formyl-6-fluorophenyl)oxybutanoic acid;
4-(2-nitro-3-formyl-6-chlorophenyl)oxybutanoic acid;
7-(3-formyl-4-nitrophenyl)oxyheptanoic acid;
7-(2-chloro-3-formyl-4-nitrophenyl)heptanoic acid;
7-(2-methyl-3-formyl-4-nitrophenyl)heptanoic acid;
7-(3-formyl-4-nitro-5-chlorophenyl)heptanoic acid;
7-(2-formyl-3-nitrophenyl)heptanoic acid;
7-(2-formyl-3-nitro-4-fluorophenyl)heptanoic acid;
7-(2-methyl-4-formyl-4-nitrophenyl)heptanoic acid;
7-(2-formyl-3-nitro-5-chlorophenyl)heptanoic acid;
7-(2-nitro-3-formylphenyl))heptanoic acid;
7-(2-nitro-3-formyl-4-fluorophenyl)heptanoic acid;
7-(2-nitro-3-formyl-6-chlorophenyl)heptanoic acid;
7-(2-nitro-3-formyl-5-methylphenyl)heptanoic acid;
7-(3-nitro-4-formylphenyl)heptanoic acid;
7-(3-nitro-4-formyl-5-methylphenyl)heptanoic acid;
5-(2-formyl-3-nitrophenyl)oxypentanoic acid;
5-(2-formyl-3-nitro-4-chlorophenyl)oxypentanoic acid;
5-(2-formyl-3-nitro-4-methylphenyl)oxypentanoic acid;
5-(2-formyl-3-nitro-6-methylphenyl)oxypentanoic acid;
5-(3-formyl-4-nitro-5-chlorophenyl)oxypentanoic acid;
5-(2-chloro-3-formyl-4-nitrophenyl)oxypentanoic acid;
5-(3-formyl-4-nitrophenyl)oxypentanoic acid;
5-(3-nitro-4-formylphenyl)oxypentanoic acid;
5-(3-nitro-4-formyl-5-methylphenyl)oxypentanoic acid;
5-(3-nitro-4-formyl-6-chlorophenyl)oxypentanoic acid;
5-(3-formyl-4-nitro-6-chlorophenyl)oxypentanoic acid;
5-(2-nitro-3-formylphenyl)oxypentanoic acid;
5-(2-nitro-3-formyl-4-methylphenyl)oxypentanoic acid;
5-(2-nitro-3-formyl-6-chlorophenyl)oxypentanoic acid;
6-(2-formyl-3-nitrophenyl)oxyhexanoic acid;
6-(2-formyl-3-nitro-4-chlorophenyl)oxyhexanoic acid;
6-(2-formyl-3-nitro-6-chlorophenyl)oxyhexanoic acid;
6-(3-formyl-4-nitrophenyl)oxyhexanoic acid;
6-(3-formyl-4-nitro-6-chlorophenyl)oxyhexanoic acid;
6-(3-formyl-4-nitro-5-methylphenyl)oxyhexanoic acid;
6-(2-nitro-3-formylphenyl)oxyhexanoic acid;
6-(2-nitro-3-formyl-6-fluorophenyl)oxyhexanoic acid;
6-(2-nitro-3-formyl-5-methylphenyl)oxyhexanoic acid;
6-(3-nitro-4-formylphenyl)oxyhexanoic acid;
6-(3-nitro-4-formyl-6-methylphenyl)oxyhexanoic acid;
6-(3-nitro-4-formyl-5-chlorophenyl)oxyhexanoic acid;
2-(2-chloro-3-formyl-4-nitrophenyl)oxyacetic acid;
2-(3-formyl-4-nitrophenyl)oxyacetic acid;
2-(3-formyl-4-nitro-5-chlorophenyl)oxyacetic acid;
2-(2-chloro-4-nitro-5-formylphenyl)oxyacetic acid; and
2-(3-formyl-4-nitro-5-fluorophenyl)oxyacetic acid.

PREPARATION 3

4-(3-formyl-4-nitrophenyl)oxybutanoic acid chloride and related compounds of Formula 5

Conversion of the acids of formula 4 to the acid halide, preferably the chloride, of formula 5 is carried out as follows.

To a stirred suspension of 4-(3-formyl-4-nitrophenyl)oxybutanoic acid (12.65 g) in benzene (50 ml) and dimethylformamide (0.5 ml) was added oxalyl chloride (4.40 ml) in small portions. When all the acid had been dissolved, the mixture was stirred for an additional 30 minutes. Evaporation of the solvent gave a thick syrup which was redissolved in dry tetrahydrofuran (50 ml) and reevaporated twice. The final residue of crude acid chloride was dissolved in tetrahydrofuran (50 ml) and used without further purification in the next reaction step.

Proceeding in a similar manner, the acids prepared in accordance with Preparation 2 are converted to the corresponding acid chloride:

4-(3-formyl-4-nitrophenyl)oxybutanoic acid chloride;
4-(3-nitro-4-formylphenyl)oxybutanoic acid chloride;
4-(2-formyl-3-nitrophenyl)oxybutanoic acid chloride;
4-(2-nitro-3-formylphenyl)oxybutanoic acid chloride;
4-(3-formyl-4-nitrophenyl)oxybutanoic acid chloride;
7-(3-formyl-4-nitrophenyl)oxyheptanoic acid chloride;
6-(3-formyl-4-nitrophenyl)oxyhexanoic acid chloride;

5-(3-formyl-4-nitrophenyl)oxypentanoic acid chloride;
4-(2-chloro-3-formyl-4-nitrophenyl)oxybutanoic acid chloride;
4-(3-formyl-4-nitro-5-chlorophenyl)oxybutanoic acid chloride;
4-(2-chloro-4-nitro-5-formylphenyl)oxybutanoic acid chloride;
4-(3-formyl-4-nitro-5-fluorophenyl)oxybutanoic acid chloride;
4-(2-fluoro-3-formyl-4-nitrophenyl)oxybutanoic acid chloride;
4-(2-methyl-3-formyl-4-nitrophenyl)oxybutanoic acid chloride;
4-(2-formyl-3-nitro-6-fluorophenyl)oxybutanoic acid chloride;
4-(2-formyl-3-nitro-4-chlorophenyl)oxybutanoic acid chloride;
4-(2-formyl-3-nitro-5-fluorophenyl)oxybutanoic acid chloride;
4-(2-formyl-3-nitrophenyl)oxybutanoic acid chloride;
4-(2-formyl-3-nitro-5-methylphenyl)oxybutanoic acid chloride;
4-(2-formyl-3-nitro-6-fluorophenyl)oxybutanoic acid chloride;
4-(2-nitro-3-formylphenyl)oxybutanoic acid chloride;
4-(2-nitro-3-formyl-5-methylphenyl)oxybutanoic acid chloride;
4-(3-nitro-4-formyl-6-fluorophenyl)oxybutanoic acid chloride;
4-(2-chloro-4-formyl-5-nitrophenyl)oxybutanoic acid chloride;
4-(3-nitro-4-formylphenyl)oxybutanoic acid chloride;
4-(3-nitro-4-formyl-5-methylphenyl)oxybutanoic acid chloride;
4-(2-nitro-3-formyl-6-fluorophenyl)oxybutanoic acid chloride;
4-(2-nitro-3-formyl-6-chlorophenyl)oxybutanoic acid chloride;
7-(3-formyl-4-nitrophenyl)oxyheptanoic acid chloride;
7-(2-chloro-3-formyl-4-nitrophenyl)heptanoic acid chloride;
7-(2-methyl-3-formyl-4-nitrophenyl)heptanoic acid chloride;
7-(3-formyl-4-nitro-5-chlorophenyl)heptanoic acid chloride;
7-(2-formyl-3-nitrophenyl)heptanoic acid chloride;
7-(2-formyl-3-nitro-4-fluorophenyl)heptanoic acid chloride;
7-(2-methyl-3-formyl-4-nitrophenyl)heptanoic acid chloride;
7-(2-formyl-3-nitro-5-chlorophenyl)heptanoic acid chloride;
7-(2-nitro-3-formylphenyl)heptanoic acid chloride;
7-(2-nitro-3-formyl-4-fluorophenyl)heptanoic acid chloride;
7-(2-nitro-3-formyl-6-chlorophenyl)heptanoic acid chloride;
7-(2-nitro-3-formyl-5-methylphenyl)heptanoic acid chloride;
7-(3-nitro-4-formylphenyl)heptanoic acid chloride;
7-(3-nitro-4-formyl-5-methylphenyl)heptanoic acid chloride;
5-(2-formyl-3-nitrophenyl)oxypentanoic acid chloride;
5-(2-formyl-3-nitro-4-chlorophenyl)oxypentanoic acid chloride;
5-(2-formyl-3-nitro-4-methylphenyl)oxypentanoic acid chloride;
5-(2-formyl-3-nitro-6-methylphenyl)oxypentanoic acid chloride;
5-(3-formyl-4-nitro-5-chlorophenyl)oxypentanoic acid chloride;
5-(2-chloro-3-formyl-4-nitrophenyl)oxypentanoic acid chloride;
5-(3-formyl-4-nitrophenyl)oxypentanoic acid chloride;
5-(3-nitro-4-formylphenyl)oxypentanoic acid chloride;
5-(3-nitro-4-formyl-5-methylphenyl)oxypentanoic acid chloride;
5-(3-nitro-4-formyl-6-chlorophenyl)oxypentanoic acid chloride;
5-(3-formyl-4-nitro-6-chlorophenyl)oxypentanoic acid chloride;
5-(2-nitro-3-formylphenyl)oxypentanoic acid chloride;
5-(2-nitro-3-formyl-4-methylphenyl)oxypentanoic acid chloride;
5-(2-nitro-3-formyl-6-chlorophenyl)oxypentanoic acid chloride;
6-(2-formyl-3-nitrophenyl)oxyhexanoic acid chloride;
6-(2-formyl-3-nitro-4-chlorophenyl)oxyhexanoic acid chloride;
6-(2-formyl-3-nitro-6-chlorophenyl)oxyhexanoic acid chloride;
6-(3-formyl-4-nitrophenyl)oxyhexanoic acid chloride;
6-(3-formyl-4-nitro-6-chlorophenyl)oxyhexanoic acid chloride;
6-(3-formyl-4-nitro-5-methylphenyl)oxyhexanoic acid chloride;
6-(2-nitro-3-formylphenyl)oxyhexanoic acid chloride;
6-(2-nitro-3-formyl-6-fluorophenyl)oxyhexanoic acid chloride;
6-(2-nitro-3-formyl-5-methylphenyl)oxyhexanoic acid chloride;
6-(3-nitro-4-formylphenyl)oxyhexanoic acid chloride;
6-(3-nitro-4-formyl-6-methylphenyl)oxyhexanoic acid chloride;
6-(3-nitro-4-formyl-5-chlorophenyl)oxyhexanoic acid chloride;
2-(2-chloro-3-formyl-4-nitrophenyl)oxyacetic acid chloride;
2-(3-formyl-4-nitrophenyl)oxyacetic acid chloride;
2-(3-formyl-4-nitro-5-chlorophenyl)oxyacetic acid chloride;
2-(2-chloro-4-nitro-5-formylphenyl)oxyacetic acid chloride; and
2-(3-formyl-4-nitro-5-fluorophenyl)oxyacetic acid.

PREPARATION 4

N-cyclohexyl-N-methyl-4-(3-formyl-4-nitrophenyl)oxybutanamide and related compounds of Formula 6

Preparation of the amides represented by Formula 6 is carried out by either of the following two steps.

A. Into a well-stirred solution of N-methyl-N-cyclohexylamine (29.5 ml) and sodium carbonate (28.8 g) in tetrahydrofuran (250 ml) and water (500 ml) cooled to 0° C. in an ice bath was added the tetrahydrofuran solution of the 4-(3-formyl-4-nitrophenyl)oxybutanoic acid chloride from Preparation 3 dropwise. When addition of the acid chloride was completed, the cooling bath was removed and the mixture allowed to stir at room temperature for 1 hour. Most of the tetrahydrofuran was removed by evaporation and the aqueous residue partitioned between ethyl acetate and saturated sodium carbonate (500 ml each). The combined organic layers were washed with additional saturated sodium carbonate (2×20 ml), water (1×100 ml), 1M HCl (2×200 ml) and with brine (2×200 ml) and dried with sodium sulfate. The ethyl acetate was evaporated to give a residue which was crystallized from ethyl acetate to give N-cyclohexyl-N-methyl-4-(3-formyl-4-nitrophenyl)oxybutanamide, (m.p. 98°–100° C.). Alternatively, the extraction residue was chromatographed on silica gel (10% ethyl acetate in dichloromethane as eluant.)

B. A tetrahydrofuran solution of 4-(3-formyl-4-nitrophenyl)oxybutanoic acid chloride was added dropwise to a solution of N-cyclohexyl-N-methylamine (60 mmol), triethylamine (9.0 ml) and 4-dimethylaminopyridine (0.6 g) in dry tetrahydrofuran (100 ml) blanketed under nitrogen and cooled to 0° C. by an ice bath. When addition of the acid chloride was complete the reaction was stirred at room temperature for 2 hours. After removal of the tetrahydrofuran, the residue was partitioned between ethyl acetate and 1M HCl (300 ml each). The organic layer was then washed with 1M HCl (2×100 ml), saturated sodium carbonate (3×100 ml) and brine (2×100 ml), dried over sodium sulfate filtered and the ethyl acetate flash evaporated. Purification of the residue was carried out as in method A above.

Using either of these procedures and substituting the appropriate secondary amine and acid chloride for those described, there may be prepared the following representative compounds:

N-cyclohexyl-N-methyl-4-(3-formyl-4-nitrophenyl)oxybutanamide;
N-cyclohexyl-N-ethyl-4-(3-nitro-4-formylphenyl)oxybutanamide;
N-cyclohexyl-N-methyl-4-(2-formyl-3-nitrophenyl)oxybutanamide;
N-cyclohexyl-N-methyl-4-(2-nitro-3-formylphenyl)oxybutanamide;
N-benzyl-N-pentyl-4-(3-formyl-4-nitrophenyl)oxybutanamide;
N-cyclohexyl-N-methyl-7-(3-formyl-4-nitrophenyl)oxyheptanamide;
N-cyclohexyl-N-methyl-6-(3-formyl-4-nitrophenyl)oxyhexanamide;
N-morpholinyl-5-(3-formyl-4-nitrophenyl)oxypentanamide;
N-cyclohexyl-N-hydroxyethyl-4-(3-formyl-4-nitrophenyl)oxybutanamide, m.p. 108°–110° C.;
N-cyclohexyl-N-hydroxyethyl-4-(2-chloro-3-formyl-4-nitrophenyl)oxybutanamide;
N-cyclohexylmethyl-N-hydroxyethyl-4-(3-formyl-4-nitro-5-chlorophenyl)oxybutanamide;
N-hexyl-N-methyl-4-(2-chloro-4-nitro-5-formylphenyl)oxybutanamide;
N,N-dimethyl-4-(3-formyl-4-nitro-5-fluorophenyl)oxybutanamide;
N-ethyl-N-methyl-4-(2-fluoro-3-formyl-4-nitrophenyl)oxybutanamide;
N-pentyl-N-methyl-4-(2-methyl-3-formyl-4-nitrophenyl)oxybutanamide;
N-hexyl-N-hydroxyethyl-4-(2-formyl-3-nitro-6-fluorophenyl)oxybutanamide;
N,N-dihexyl-4-(2-formyl-3-nitro-4-chlorophenyl)oxybutanamide;
N,N-dipentyl-4-(2-formyl-3-nitro-5-fluorophenyl)oxybutanamide;
N-cyclohexyl-N-6-hydroxyhexyl-4-(2-formyl-3-nitrophenyl)oxybutanamide;
N-cyclohexyl-N-n-hexyl-4-(2-formyl-3-nitro-5-methylphenyl)-oxybutanamide;
N-cyclopentyl-N-methyl-4-(2-formyl-3-nitro-6-fluorophenyl)-oxybutanamide;
N-cyclopropylmethyl-N-methyl-4-(2-nitro-3-formylphenyl)oxybutanamide;
N-cycloheptyl-N-methyl-4-(2-nitro-3-formyl-5-methylphenyl)oxybutanamide;
N-cyclopentylbutyl-N-methyl-4-(3-nitro-4-formyl-6-fluorophenyl)oxybutanamide;
N-cyclopentylmethyl-N-methyl-4-(2-chloro-4-formyl-5-nitrophenyl)oxybutanamide;
N-cyclopentyl-N-butyl-4-(3-nitro-4-formylphenyl)oxybutanamide;
N-cyclopentyl-N-hydroxyethyl-4-(3-nitro-4-formyl-5-methylphenyl)oxybutanamide;
N-cyclopentylmethyl-N-hydroxyethyl-4-(2-nitro-3-formyl-6-fluorophenyl)oxybutanamide;
N-cyclopentylbutyl-N-hydroxyethyl-4-(2-nitro-3-formyl-6-chlorophenyl)oxybutanamide;
N,N-dicyclohexyl-4-(3-formyl-4-nitrophenyl)oxybutanamide, m.p. 107°–108° C.;
N-cyclohexyl-N-4-hydroxy-n-butyl-7-(2-chloro-3-formyl-4-nitrophenyl)oxyheptanamide;
N-phenyl-N-methyl-7-(2-methyl-3-formyl-4-nitrophenyl)oxyheptanamide;
N-phenyl-N-methyl-4-(3-formyl-4-nitrophenyl)oxybutanamide, m.p. 72°–73° C.;
N-phenyl-N-hexyl-7-(3-formyl-4-nitro-5-chlorophenyl)oxyheptanamide;
N-phenyl-N-6-hydroxyhexyl-7-(2-formyl-3-nitrophenyl)oxyheptanamide;
N-cyclohexyl-N-n-butyl-7-(2-formyl-3-nitro-4-fluorophenyl)oxyheptanamide;
N-benzyl-N-methyl-7-(2-methyl-3-formyl-4-nitrophenyl)oxyheptanamide;
N-benzyl-N-methyl-4-(3-formyl-4-nitrophenyl)oxybutanamide, syrup;
N,N-dibenzyl-7-(2-formyl-3-nitro-5-chlorophenyl)oxyheptanamide;
N,N-dibenzyl-4-(3-formyl-4-nitrophenyl)oxybutanamide, m.p. 76°–77° C.;
N-diphenylmethyl-N-methyl-7-(2-nitro-3-formylphenyl)oxyheptanamide;
N-diphenylmethyl-N-methyl-4-(3-formyl-4-nitrophenyl)oxybutanamide, m.p. 117°–118° C.;
morpholinyl-4-(3-formyl-4-nitrophenyl)oxybutanamide, m.p. 106°–107° C.;
morpholinyl-7-(2-nitro-3-formyl-4-fluorophenyl)oxyheptanamide;
piperidinyl-7-(2-nitro-3-formyl-6-chlorophenyl)oxyheptanamide;
piperidinyl-4-(3-formyl-4-nitrophenyl)oxybutanamide, m.p. 98°–99° C.;
pyrrolidinyl-7-(2-nitro-3-formyl-5-methylphenyl)oxyheptanamide;
pyrrolidinyl-4-(3-formyl-4-nitrophenyl)oxybutanamide, m.p. 82°–83° C.;
N-methylpiperazinyl-7-(3-nitro-4-formylphenyl)oxyheptanamide;
tetrahydroquinolinyl-7-(3-nitro-4-formyl-5-methylphenyl)oxyheptanamide;

tetrahydroquinolinyl-4-(3-formyl-4-nitrophenyl)ox-
ybutanamide, m.p. 95°-96° C.;
tetrahydroisoquinolinyl-7-(2-formyl-3-nitrophenyl-
)oxyheptanamide;
tetrahydroisoquinolinyl-4-(3-formyl-4-nitrophenyl-
)oxybutanamide, m.p. 99°-100° C.;
indolinyl-5-(2-formyl-3-nitro-4-chlorophenyl)ox-
ypentanamide;
indolinyl-4-(3-formyl-4-nitrophenyl)oxybutanamide,
m.p. 155°-156° C.;
(±)-decahydroquinolinyl-5-(2-formyl-3-nitro-4-
methylphenyl)oxypentanamide;
N-cyclohexyl-N-hydroxyethyl-5-(2-formyl-3-nitro-6-
methylphenyl)oxypentanamide;
N-cyclohexyl-N-methyl-5-(3-formyl-4-nitro-5-
chlorophenyl)oxypentanamide;
N-cyclohexyl-N-4-hydroxy-n-butyl-5-(2-chloro-3-
formyl-4-nitro-phenyl)oxypentanamide;
N-cyclohexyl-N-n-hexyl-5-(3-formyl-4-nitrophenyl-
)oxypentanamide;
N-phenyl-N-methyl-5-(3-nitro-4-formylphenyl)ox-
ypentanamide;
N-benzyl-N-methyl-5-(3-nitro-4-formyl-5-methyl-
phenyl)oxypentanamide;
N,N-dibenzyl-5-(3-nitro-4-formyl-6-chlorophenyl-
)oxypentanamide;
N,N-dicyclohexyl-5-(3-formyl-4-nitro-6-chloro-
phenyl)oxypentanamide;
(±)-decahydroquinolinyl-5-(2-nitro-3-formylphenyl-
)oxypentanamide;
N-cyclohexyl-N-hydroxyethyl-5-(2-nitro-3-formyl-4-
methylphenyl)oxypentanamide;
N-phenyl-N-methyl-5-(2-nitro-3-formyl-6-chloro-
phenyl)oxypentanamide;
N-cyclohexyl-N-methyl-6-(2-formyl-3-nitrophenyl-
)oxyhexanamide;
N-benzyl-N-methyl-6-(2-formyl-3-nitro-4-chloro-
phenyl)oxyhexanamide;
N,N-dibenzyl-6-(2-formyl-3-nitro-6-chlorophenyl-
)oxyhexanamide;
N,N-dicyclohexyl-6-(3-formyl-4-nitrophenyl)ox-
yhexanamide;
(±)-decahydroquinolinyl-6-(3-formyl-4-nitro-6-
chlorophenyl)oxyhexanamide;
N-diphenylmethyl-N-methyl-6-(3-formyl-4-nitro-5-
methyl-phenyl)oxyhexanamide;
N-cyclohexyl-N-hydroxyethyl-6-(2-nitro-3-formyl-
phenyl)oxyhexanamide;
N-cyclohexyl-N-methyl-6-(2-nitro-3-formyl-6-fluoro-
phenyl)oxyhexanamide;
N-phenyl-N-methyl-6-(2-nitro-3-formyl-5-methyl-
phenyl)oxyhexanamide;
N-benzyl-N-methyl-6-(3-nitro-4-formylphenyl)ox-
yhexanamide;
N,N-dibenzyl-6-(3-nitro-4-formyl-6-methylphenyl-
)oxyhexanamide;
N,N-dicyclohexyl-6-(3-nitro-4-formyl-5-chloro-
phenyl)oxyhexanamide;
(±)-decahydroquinolinyl-2-(2-chloro-3-formyl-4-
nitrophenyl)oxyacetamide;
N-diphenylmethyl-N-methyl-2-(3-formyl-4-nitro-
phenyl)oxyacetamide;
N-cyclohexyl-N-hydroxyethyl-2-(3-formyl-4-nitro-5-
chlorophenyl)acetamide;
N-cyclohexyl-N-n-hexyl-2-(2-chloro-4-nitro-5-for-
mylphenyl)oxyacetamide; and
N-benzyl-N-methyl-2-(3-formyl-4-nitro-5-fluoro-
phenyl)oxyactamide.

PREPARATION 5

N-Cyclohexyl-N-methyl-4-(3-(1-hydroxyeth-1-yl)-4-
nitrophenyl)oxybutanamide and related compounds of
Formula 7

Compounds of Formula 7 wherein $R_1$ is alkyl and A
does not contain an hydroxyalkyl group are prepared
by a two step process, the first step of which is as fol-
lows.

Into a tetrahydrofuran solution of methyl Grignard
reagent (120 mmol), either purchased from commercial
sources or freshly generated from the corresponding
halide and elemental magnesium, was added dropwise a
solution of nitroaldehyde (35 g) in tetrahydrofuran (200
ml). The resulting mixture was warmed to reflux for one
hour, then cooled and quenched with saturated aqueous
ammonium chloride. Evaporation of the tetrahydrofu-
ran followed by extraction with ethyl acetate provided
N-cyclohexyl-N-methyl-4-(3-(1-hydroxyeth-1-yl)-4-
nitrophenyl)oxybutanamide.

Proceeding in a similar manner, but substituting the
the appropriate reagents and an alkylamide whose prep-
aration is described in Preparation 4, there are prepared
the following exemplary alcohols:
N-cyclohexyl-N-methyl-4-(3-(1-hydroxybut-1-yl)-4-
nitrophenyl)oxybutanamide;
N-cyclohexyl-N-ethyl-4-(3-nitro-4-(1-hydroxyprop-
1-yl)phenyl)oxybutanamide;
N-cyclohexyl-N-methyl-4-(2-(1-hydroxyeth-1-yl)-3-
nitrophenyl)oxybutanamide;
N-cyclohexyl-N-methyl-4-(2-nitro-3-(1-hydroxyeth-
1-yl)phenyl)oxybutanamide;
N-benzyl-N-pentyl-4-(3-(1-hydroxeth-1-yl)-4-nitro-
phenyl)oxybutanamide;
N-cyclohexyl-N-methyl-5-(3-(1-hydroxyeth-1-yl)-4-
nitrophenyl)oxyheptanamide;
N-cyclohexyl-N-methyl-6-(3-(1-hydroxyeth-1-yl)-4-
nitrophenyloxyhexanamide;
N-morpholinyl-5-(3-(1-hydroxyeth-1-yl)-4-nitro-
phenyl)oxypentanamide.
N-hexyl-N-methyl-4-(2-chloro-4-nitro-5-(1-hydrox-
yeth-1-yl)phenyl)oxybutanamide;
N,N-dimethyl-4-(3-(1-hydroxyeth-1-yl)-4-nitro-5-
fluorophenyl)oxybutanamide;
N-ethyl-N-methyl-4-(2-fluoro-3-(1-hydroxyeth-1-yl)-
4-nitrophenyl)oxybutanamide;
N-pentyl-N-methyl-4-(2-methyl-3-(1-hydroxyeth-1-
yl)-4-nitrophenyl)oxybutanamide;
N,N-dihexyl-4-(2-(1-hydroxyeth-1-yl)-3-nitro-4-
chlorophenyl)oxybutanamide;
N,N-dipentyl-4-(2-(1-hydroxyeth-1-yl)-3-nitro-5-
fluorophenyl)oxybutanamide;
N-cyclohexyl-N-n-hexyl-4-(2-(1-hydroxyeth-1-yl)-3-
nitro-5-methylphenyl)-oxybutanamide;
N-cyclopentyl-N-methyl-4-(2-(1-hydroxyeth-1-yl)-3-
nitro-6-fluorophenyl)-oxybutanamide;
N-cyclopropylmethyl-N-methyl-4-(2-nitro-3-(1-
hydroxyeth-1-yl)phenyl)oxybutanamide;
N-cycloheptyl-N-methyl-4-(2-nitro-3-(1-hydroxyeth-
1-yl)-5-methylphenyl)oxybutanamide;
N-cyclopentylbutyl-N-methyl-4-(3-nitro-4-(1-
hydroxyeth-1-yl)-6-fluorophenyl)oxybutanamide;
N-cyclopentylmethyl-N-methyl-4-(2-chloro-4-(1-
hydroxyeth-1-yl)-5-nitrophenyl)oxybutanamide;
N-cyclopentyl-N-butyl-4-(3-nitro-4-(1-hydroxyeth-1-
yl)phenyl)oxybutanamide;

N,N-dicyclohexyl-4-(3-(1-hydroxyeth-1-yl)-4-nitrophenyl)oxybutanamide;
N-phenyl-N-methyl-7-(2-methyl-3-(1-hydroxyeth-1-yl)-4-nitrophenyl)oxyheptanamide;
N-phenyl-N-methyl-4-(3-(1-hydroxyeth-1-yl)-4-nitrophenyl)oxybutanamide;
N-phenyl-N-hexyl-7-(3-(1-hydroxyeth-1-yl)-4-nitro-5-chlorophenyl)oxyheptanamide;
N-phenyl-N-6-hydroxyhexyl-7-(2-(1-hydroxyeth-1-yl)-3-nitrophenyl)oxyheptanamide;
N-cyclohexyl-N-n-butyl-7-(2-(1-hydroxyeth-1-yl)-3-nitro-4-fluorophenyl)oxyheptanamide;
N-benzyl-N-methyl-7-(2-methyl-3-(1-hydroxyeth-1-yl)-4-nitrophenyl)oxyheptanamide;
N-benzyl-N-methyl-4-(3-(1-hydroxyeth-1-yl)-4-nitrophenyl)oxybutanamide;
N,N-dibenzyl-7-(2-(1-hydroxyeth-1-yl)-3-nitro-5-chlorophenyl)oxyheptanamide;
N,N-dibenzyl-4-(3-(1-hydroxyeth-1-yl)-4-nitrophenyl)oxybutanamide;
N-diphenylmethyl-N-methyl-7-(2-nitro-3-(1-hydroxyeth-1-yl)phenyl)oxyheptanamide;
N-diphenylmethyl-N-methyl-4-(3-(1-hydroxyeth-1-yl)-4-nitrophenyl)oxybutanamide;
morpholinyl-4-(3-(1-hydroxyeth-1-yl)-4-nitrophenyl)oxybutanamide;
morpholinyl-7-(2-nitro-3-(1-hydroxyeth-1-yl)-4-fluorophenyl)oxyheptanamide;
piperidinyl-7-(2-nitro-3-(1-hydroxyeth-1-yl)-6-chlorophenyl)oxyheptanamide;
piperidinyl-4-(3-(1-hydroxyeth-1-yl)-4-nitrophenyl)oxybutanamide;
pyrrolidinyl-7-(2-nitro-3-(1-hydroxyeth-1-yl)-5-methylphenyl)oxyheptanamide;
pyrrolidinyl-4-(3-(1-hydroxyeth-1-yl)-4-nitrophenyl)oxybutanamide;
N-methylpiperazinyl-7-(3-nitro-4-(1-hydroxyeth-1-yl)phenyl)oxyheptanamide;
tetrahydroquinolinyl-7-(3-nitro-4-(1-hydroxyeth-1-yl)-5-methylphenyl)oxyheptanamide;
tetrahydroquinolinyl-4-(3-(1-hydroxyeth-1-yl)-4-nitrophenyl)oxybutanamide;
tetrahydroisoquinolinyl-7-(2-(1-hydroxyeth-1-yl)-3-nitrophenyl)oxyheptanamide;
tetrahydroisoquinolinyl-4-(3-(1-hydroxyeth-1-yl)-4-nitrophenyl)oxybutanamide;
indolinyl-5-(2-(1-hydroxyeth-1-yl)-3-nitro-4-chlorophenyl)oxypentanamide;
indolinyl-4-(3-(1-hydroxyeth-1-yl)-4-nitrophenyl)oxybutanamide;
(±)-decahydroquinolinyl-5-(2-(1-hydroxyeth-1-yl)-3-nitro-4-methylphenyl)oxypentanamide;
N-cyclohexyl-N-methyl-5-(3-(1-hydroxyeth-1-yl)-4-nitro-5-chlorophenyl)oxypentanamide;
N-cyclohexyl-N-4-hydroxy-n-butyl-5-(2-chloro-3-(1-hydroxyeth-1-yl)-4-nitro-phenyl)oxypentanamide;
N-cyclohexyl-N-n-hexyl-5-(3-(1-hydroxyeth-1-yl)-4-nitrophenyl)oxypentanamide;
N-phenyl-N-methyl-5-(3-nitro-4-(1-hydroxyeth-1-yl)phenyl)oxypentanamide;
N-benzyl-N-methyl-5-(3-nitro-4-(1-hydroxyeth-1-yl)-5-methylphenyl)-oxypentanamide;
N,N-dibenzyl-5-(3-nitro-4-(1-hydroxyeth-1-yl)-6-chlorophenyl)oxypentanamide;
N,N-dicyclohexyl-5-(3-(1-hydroxyeth-1-yl)-4-nitro-6-chlorophenyl)oxypentanamide;
(±)-decahydroquinolinyl-5-(2-nitro-3-(1-hydroxyeth-1-yl)phenyl)oxypentanamide;
N-phenyl-N-methyl-5-(2-nitro-3-(1-hydroxyeth-1-yl)-6-chlorophenyl)-oxypentanamide;
N-cyclohexyl-N-methyl-6-(2-(1-hydroxyeth-1-yl)-3-nitrophenyl)oxyhexanamide;
N-benzyl-N-methyl-6-(2-(1-hydroxyeth-1-yl)-3-nitro-4-chlorophenyl)oxyhexanamide;
N,N-dibenzyl-6-(2-(1-hydroxyeth-1-yl)-3-nitro-6-chlorophenyl)oxyhexanamide;
N,N-dicyclohexyl-6-(3-(1-hydroxyeth-1-yl)-4-nitrophenyl)oxyhexanamide;
(±)-decahydroquinolinyl-6-(3-(1-hydroxyeth-1-yl)-4-nitro-6-chlorophenyl)oxyhexanamide;
N-diphenylmethyl-N-methyl-6-(3-(1-hydroxyeth-1-yl)-4-nitro-5-methyl-phenyl)oxyhexanamide;
N-cyclohexyl-N-methyl-6-(2-nitro-3-(1-hydroxyeth-1-yl)-6-fluorophenyl)oxyhexanamide;
N-phenyl-N-methyl-6-(2-nitro-3-(1-hydroxyeth-1-yl)-5-methylphenyl)oxyhexanamide;
N-benzyl-N-methyl-6-(3-nitro-4-(1-hydroxyeth-1-yl)phenyl)oxyhexanamide;
N,N-dibenzyl-6-(3-nitro-4-(1-hydroxyeth-1-yl)-6-methylphenyl)oxyhexanamide;
N,N-dicyclohexyl-6-(3-nitro-4-(1-hydroxyeth-1-yl)-5-chlorophenyl)oxyhexanamide;
(±)-decahydroquinolinyl-2-(2-chloro-3-(1-hydroxyeth-1-yl)-4-nitrophenyl)oxyacetamide;
N-diphenylmethyl-N-methyl-2-(3-(1-hydroxyeth-1-yl)-4-nitrophenyl)oxyacetamide;
N-cyclohexyl-N-n-hexyl-2-(2-chloro-4-nitro-5-(1-hydroxyeth-1-yl)phenyl)oxyacetamide; and
N-benzyl-N-methyl-2-(3-(1-hydroxyeth-1-yl)-4-nitro-5-fluorophenyl)oxyacetamide.

PREPARATION 6

N-Cyclohexyl-N-methyl-4-(3-(1-oxyeth-1-yl)-4-nitrophenyl)oxybutanamide and related compounds of Formula 8

Oxidation of the secondary alcohols for Preparation 5 is carried out by the following method to give the compounds of Formula 8.

Anhydrous chromium trioxide, 8 g, was added to a stirred solution of 60 ml of dry pyridine in 200 ml of dry dichloromethane and stirred under a dry nitrogen atmosphere at about 20° C. for 15 minutes. A solution of 27 g of N-cyclohexyl-N-methyl-4-(3-(1-hydroxyeth-1-yl)-4-nitrophenyl)oxybutanamide in 150 ml of dry dichloromethane was added and the reaction mixture stirred for an additional 30 minutes at room temperature. The solution was decanted from the residue and the residue washed with two 100 ml portions of dry diethyl ether. The organic solutions are combined, washed successively with two 200 ml portions of water and dried over anhydrous sodium sulphate. Evaporation of the solvent under reduced pressure gives a residue which is crystallized from ethyl acetate to give N-cyclohexyl-N-methyl-4-[(3-oxoeth-1-yl)-4-nitrophenyl)oxy]-butanamide.

Proceeding in a similar manner, the secondary alcohols of Preparation 5 may be converted to the corresponding ketones using the above reagents but substituting the appropriate secondary alcohol for N-cyclohexyl-N-methyl-4-(3-(1-hydroxyeth-1-yl)-4-nitrophenyl)oxybutanamide. Examples are:
N-cyclohexyl-N-methyl-4-(3-(1-oxobut-1-yl)-4-nitrophenyl)oxybutanamide;
N-cyclohexyl-N-ethyl-4-(3-nitro-4-(1oxoprop-1-yl)phenyl)oxybutanamide;

N-cyclohexyl-N-methyl-4-(2-(1-oxoeth-1-yl)-3-nitrophenyl)oxybutanamide;
N-cyclohexyl-N-methyl-4-(2-nitro-3-(1-oxoeth-1-yl)phenyl)oxybutanamide;
N-benzyl-N-pentyl-4-(3-(1-oxoxeth-1-yl)-4-nitrophenyl)oxybutanamide;
N-cyclohexyl-N-methyl-5-(3-(1-oxoeth-1-yl)-4-nitrophenyl)oxyheptanamide;
N-cyclohexyl-N-methyl-6-(3-(1-oxoeth-1-yl)-4-nitrophenyloxyhexanamide;
N-morpholinyl-5-(3-(1-oxoeth--yl)-4-nitrophenyl)oxypentanamide;
N-hexyl-N-methyl-4-(2-chloro-4-nitro-5-(1-oxoeth-1-yl)phenyl)oxybutanamide;
N,N-dimethyl-4-(3-(1-oxoeth-1-yl)-4-nitro-5-fluorophenyl)oxybutanamide
N-ethyl-N-methyl-4-(2-fluoro-3-(1-oxoeth-1-yl)-4-nitrophenyl)oxybutanamide;
N-pentyl-N-methyl-4-(2-methyl-3-(1-oxoeth-1-yl)-4-nitrophenyl)oxybutanamide;
N,N-dihexyl-4-(2-(1-oxoeth-1-yl)-3-nitro-4-chlorophenyl)oxybutanamide;
N,N-dipentyl-4-(2-(1-oxoeth-1-yl)-3-nitro-5-fluorophenyl)oxybutanamide;
N-cyclohexyl-N-6-hydroxyhexyl-4-(2-(1-oxoeth-1-yl)-3-nitrophenyl)oxybutanamide;
N-cyclohexyl-N-n-hexyl-4-(2-(1-oxoeth-1-yl)-3-nitro-5-methylphenyl)-oxybutanamide;
N-cyclopentyl-N-methyl-4-(2-(1-oxoeth-1-yl)-3-nitro-6-fluorophenyl)-oxybutanamide;
N-cyclopropylmethyl-N-methyl-4-(2-nitro-3-(1-oxoeth-1-yl)phenyl)oxybutanamide;
N-cycloheptyl-N-methyl-4-(2-nitro-3-(1-oxoeth-1-yl)-5-methylphenyl)oxybutanamide;
N-cyclopentylbutyl-N-methyl-4-(3-nitro-4-(1-hydroxyeth-1-yl)-6-fluorophenyl)oxybutanamide;
N-cyclopentylmethyl-N-methyl-4-(2-chloro-4-(1-hydroxyeth-1-yl)-5-nitrophenyl)oxybutanamide;
N-cyclopentyl-N-butyl-4-(3-nitro-4-(1-oxoeth-1-yl)phenyl)oxybutanamide;
N,N-dicyclohexyl-4-(3-(1-oxoeth-1-yl)-4-nitrophenyl)oxybutanamide;
7-(3-(1-oxoeth-1-yl)-4-nitrophenyl)oxyheptanoic acid chloride;
N-cyclohexyl-N-4-hydroxy-n-butyl-7-(2-chloro-3-(1-hydroxyeth-1-yl)-4-nitrophenyl)oxyheptanamide;
N-phenyl-N-methyl-7-(2-methyl-3-(1-oxoeth-1-yl)-4-nitrophenyl)oxyheptanamide;
N-phenyl-N-methyl-4-(3-oxoeth-1-yl)-4-nitrophenyl)oxybutanamide;
N-phenyl-N-hexyl-7-(3-(1-oxoeth-1-yl)-4-nitro-5-chlorophenyl)oxyheptanamide;
N-phenyl-N-6-hydroxyhexyl-7-(2-(1-oxoeth-1-yl)-3-nitrophenyl)oxyheptanamide;
N-cyclohexyl-N-n-butyl-7-(2-(1-oxoeth-1-yl)-3-nitro-4-fluorophenyl)oxyheptanamide;
N-benzyl-N-methyl-7-(2-methyl-3-(1-oxoeth-1-yl)-4-nitrophenyl)oxyheptanamide;
N-benzyl-N-methyl-4-(3-(1-oxoeth-1-yl)-4-nitrophenyl)oxybutanamide;
N,N-dibenzyl-7-(2-(1-oxoeth-1-yl)-3-nitro-5-chlorophenyl)oxyheptanamide;
N,N-dibenzyl-4-(3-(1-oxoeth-1-yl)-4-nitrophenyl)oxybutanamide;
N-diphenylmethyl-N-methyl-7-(2-nitro-3-(1-oxoeth-1-yl)phenyl)oxyheptanamide;
N-diphenylmethyl-N-methyl-4-(3-(1-oxoeth-1-yl)-4-nitrophenyl)oxybutanamide;

morpholinyl-4-(3-(1-oxoeth-1-yl)-4-nitrophenyl)oxybutanamide;
morpholinyl-7-(2-nitro-3-(1-oxoeth-1-yl)-4-fluorophenyl)oxyheptanamide;
piperidinyl-7-(2-nitro-3-(1-oxoeth-1-yl)-6-chlorophenyl)oxyheptanamide;
piperidinyl-4-(3-(1-oxoeth-1-yl)-4-nitrophenyl)oxybutanamide;
pyrrolidinyl-7-(2-nitro-3-(1-oxoeth-1-yl)-5-methylphenyl)oxyheptanamide;
pyrrolidinyl-4-(3-(1-oxoeth-1-yl)-4-nitrophenyl)oxybutanamide;
N-methylpiperazinyl-7-(3-nitro-4-(1-oxoeth-1-yl)phenyl)oxyheptanamide;
tetrahydroquinolinyl-7-(3-nitro-4-(1-oxoeth-1-yl)-5-methylphenyl)oxyheptanamide;
tetrahydroquinolinyl-4-(3-(1-oxoeth-1-yl)-4-nitrophenyl)oxybutanamide;
tetrahydroisoquinolinyl-7-(2-(1-oxoeth-1-yl)-3-nitrophenyl)oxyheptanamide;
tetrahydroisoquinolinyl-4-(3-(1-oxoeth-1-yl)-4-nitrophenyl)oxybutanamide;
indolinyl-5-(2-(1-oxoeth-1-yl)-3-nitro-4-chlorophenyl)oxypentanamide;
indolinyl-4-(3-(1-oxoeth-1-yl)-4-nitrophenyl)oxybutanamide;
(±)-decahydroquinolinyl-5-(2-(1-oxoeth-1-yl)-3-nitro-4-methylphenyl)oxypentanamide;
N-cyclohexyl-N-methyl-5-(3-(1-oxoeth-1-yl)-4-nitro-5-chlorophenyl)oxypentanamide;
N-cyclohexyl-N-4-hydroxy-n-butyl-5-(2-chloro-3-(1-hydroxyeth-1-yl)-4-nitro-phenyl)oxypentanamide;
N-cyclohexyl-N-n-hexyl-5-(3-(1-oxoeth-1-yl)-4-nitrophenyl)oxypentanamide;
N-phenyl-N-methyl-5-(3-nitro-4-(1-oxoeth-1-yl)phenyl)oxypentanamide
N-benzyl-N-methyl-5-(3-nitro-4-(1-oxoeth-1-yl)-5-methylphenyl)-oxypentanamide;
N,N-dibenzyl-5-(3-nitro-4-(1-oxoeth-1-yl)-6-chlorophenyl)oxypentanamide;
N,N-dicyclohexyl-5-(3-(1-oxoeth-1-yl)-4-nitro-6-chlorophenyl)oxypentanamide;
(±)-decahydroquinolinyl-5-(2-nitro-3-(1-oxoeth-1-yl)phenyl)oxypentanamide;
N-phenyl-N-methyl-5-(2-nitro-3-(1-oxoeth-1-yl)-6-chlorophenyl)-oxypentanamide;
N-cyclohexyl-N-methyl-6-(2-(1-oxoeth-1-yl)-b 3-nitrophenyl)oxyhexanamide;
N-benzyl-N-methyl-6-(2-(1-oxoeth-1-yl)-3-nitro-4-chlorophenyl)-oxyhexanamide;
N,N-dibenzyl-6-(2-(1-oxoeth-1-yl)-3-nitro-6-chlorophenyl)oxyhexanamide;
N,N-dicycohexyl-6-(3-(1-oxoeth-1-yl)-4-nitrophenyl)oxyhexanamide;
(±)-decayhydroquinolinyl-6-(3-(1-oxoeth-1-yl)-4-nitro-6-chlorophenyl)oxyhexanamide;
N-diphenylmethyl-N-methyl-6-(3-(1-oxoeth-1-yl)-4-nitro-5-methyl-phenyl)oxyhexanamide;
N-cyclohexyl-N-methyl-6-(2-nitro-3-(1-oxoeth-1-yl)-6-fluorophenyl)oxyhexanamide;
N-phenyl-N-methyl-6-(2-nitro-3-(1-oxoeth-1-yl)-5-methylphenyl)oxyhexanamide;
N-benzyl-N-methyl-6-(3-nitro-4-(1-oxoeth-1-yl)phenyl)oxyhexanamide;
N,N-dibenzyl-6-(3-nitro-4-(1-oxoeth-1-yl)-6-methylphenyl)oxyhexanamide;
N,N-dicyclohexyl-6-(3-nitro-4-(1-oxoeth-1-yl)-5-chlorophenyl)oxyhexanamide;

(±)-decahydroquinolinyl-2-(2-chloro-3-(1-oxoeth-1-yl)-4-nitrophenyl)oxyacetamide;
N-diphenylmethyl-N-methyl-2-(3-(1-oxoeth-1-yl)-4-nitrophenyl)oxyacetamide;
N-cyclohexyl-N-n-hexyl-2-(2-chloro-4-nitro-5-(1-hydroxyeth-1-yl)phenyl)oxyacetamide; and
N-benzyl-N-methyl-2-(3-(1-oxoeth-1-yl)-4-nitro-5-fluorophenyl)oxyacetamide.

PREPARATION 7

N-cyclohexyl-N-(2-acetoxyethyl)-4-(4-nitro-3-formylphenyl)oxybutanamide and related compounds of Formula 6

Compounds wherein $R_1$ is alkyl and A comprises a hydroxyalkyl group must be protected at the hydroxyl moiety before introduction of $R_1$ and oxidation. In these cases, a compound of formula (6), wherein A comprises a free hydroxyl group, is reacted with an aliphatic or aromatic acyl anhydride in pyridine according to the following method.

Into a solution of N-cyclohexyl-N-(2-hydroxyethyl)-4-(4-nitro-3-formylphenyl)-oxybutanamide (18.9 g, 50 mmol) in pyridine (100 ml), was added acetic acid anhydride (20 ml). After stirring for about one hour at room temperature, the mixture was evaporated, and the residue was partitioned between ethyl acetate and water (200 ml each O. The organic layer was sequentially washed with water (2×100 ml), 1M HCl (3×100 ml), saturated aqueous sodium bicarbonate (3×100 ml) and brine (2×100 ml); and then it was dried and evaporated to give N-cyclohexyl-N-(2-acetoxyethyl)-4-(4-nitro-3-formylphenyl)oxybutanamide, as a thick amber syrup. Similarly, by substitution of the appropriate acyl anhydride for acetic anhydride, and the desired hydroxyalkyl-substituted amide for the above-noted hydroxyethyl amide, the following compounds are prepared:

N-cyclohexyl-N-acetoxypropyl-4-(3-formyl-4-nitrophenyl)oxybutanamide;
N-cyclohexyl-N-acetoxyethyl-4-(3-nitro-4-formylphenyl)oxybutanamide;
N-cyclohexyl-N-acetoxybutyl-4-(2-formyl-3-nitrophenyl)oxybutanamide;
N-cyclohexyl-N-acetoxypentyl-4-(2-nitro-3-formylphenyl)oxybutanamide;
N-benzyl-N-(5-acetoxypentyl)-4-(3-formyl-4-nitrophenyl)oxybutanamide;
N-cyclohexyl-N-acetoxyhexyl-7-(3-formyl-4-nitrophenyl)oxyheptanamide;
N-cyclohexyl-N-acetoxypropyl-6-(3-formyl-4-nitrophenyl)oxyhexanamide;
N-cyclohexyl-N-(2-acetoxyethyl)-4-(3-formyl-4-nitrophenyl)oxybutanamide;
N-cyclohexyl-N-(2-acetoxyethyl)-4-(2-chloro-3-formyl-4-nitrophenyl)oxybutanamide;
N-cyclohexylmethyl-N-(2-acetoxypethyl)-4-(3-formyl-4-nitro-5-chlorophenyl)oxybutanamide;
N-hexyl-N-(2-acetoxyethyl)-4-(2-formyl-3-nitro-6-fluorophenyl)oxybutanamide;
N-cyclohexyl-N-(6-acetoxyhexyl)-4-(2-formyl-3-nitrophenyl)oxybutanamide;
N-cyclopentyl-N-(2-acetoxyethyl)-4-(3-nitro-4-formyl-5-methylphenyl)oxybutanamide;
N-cyclopentylmethyl-N-(2-acetoxyethyl)-4-(2-nitro-3-formyl-6-fluorophenyl)oxybutanamide;
N-cyclopentylbutyl-N-(2-acetoxyethyl)-4-(2-nitro-3-formyl-6-chlorophenyl)oxybutanamide;
N-cyclohexyl-N-(2-acetoxyethyl)-5-(2-formyl-3-nitro-6-methylphenyl)oxypentanamide;
N-cyclohexyl-N-(4-acetoxy-n-butyl)-7-(2-chloro-3-formyl-4-nitrophenyl)oxyheptanamide;
N-cyclohexyl-N-(2-acetoxyethyl)-5-(2-nitro-3-formyl-4-methylphenyl)oxypentanamide;
N-cyclohexyl-N-(2-acetoxyethyl)-6-(2-nitro-3-formylphenyl)oxyhexanamide; and
N-cyclohexyl-N-(2-acetoxyethyl)-2-(3-formyl-4-nitro-5-chlorophenyl)oxyacetamide.

PREPARATION 8

N-cyclohexyl-N-(2-acetoxyethyl)-4-(4-nitro-3-(1-hydroxyeth-1-yl)phenyl)oxybutanamide and related compounds of Formula 7

Addition of the $R_1$ substituent to the protected aldehydes of preparation 7 may be carried out according to the procedure described in preparation 5. So long as particular care is paid to temperature control and the use of a stoichiometric amount of alkyl grignard, reasonable selectivity of attack at the formyl group is attained. Alternatively, use of a modified titanium IV reagent, e.g., methyl triisopropoxy titanium, will selectively afford the desired carbinol without side reaction. As an example of this later synthetic transformation, the protected aldehyde described in preparation 7 is transformed into the corresponding ethyl alcohol.

An ethereal solution of methyl triisopropoxy titanium (60 mmol), prepared in situ according to the method described by Seebach et al. (Modern Synthetic Methods, Vol. 3, Wiley, New York, N.Y., 1983, p. 224; Helv. Chem. Acta, 64, 357 (1981)) was added portionwise to a solution of N-cyclohexyl-N-(2-acetoxyethyl)-4-nitro-3-formylphenyl)oxybutanamide (50 mmol) in dry tetrahydrofuran (THF, 250 ml) under a blanket of nitrogen. After about 1 hour at room temperature, the mixture was evaporated, and the residue was dissolved in ethyl acetate. The organic layer was washed with 1M HCl (3×100 ml) and brine (2×100 ml), dried, filtered and evaporated to give N-cyclohexyl-N-(2-acetoxyethyl)-4-(4-nitro-3(1-hydroxyethyl)phenyl)oxybutanamide as a thick amber syrup.

Similarly, by substituting the appropriate alkyl of aryl titanium (IV) reagent for methyl triisopropoxy titanium, and using the desired aldehyde of formula (6) as prepared by Preparation 7, the following compounds are obtained:

N-cyclohexyl-N-acetoxypropyl-4-(3-(1-hydroxyeth-1-yl)-4-nitrophenyl)oxybutanamide;
N-cyclohexyl-N-acetoxyethyl-4-(3-nitro-4-(1-hydroxyeth-1-yl)phenyl)oxybutanamide;
N-cyclohexyl-N-acetoxybutyl-4-(2-(1-hydroxyeth-1-yl)-3-nitrophenyl)oxybutanamide;
N-cyclohexyl-N-acetoxypentyl-4-(2-nitro-3-(1-hydroxyeth-1-yl)phenyl)oxybutanamide;
N-benzyl-N-(5-acetoxypentyl)-4-(3-(1-hydroxyeth-1-yl)-4-nitrophenyl)oxybutanamide;
N-cyclohexyl-N-acetoxyhexyl-7-(3-(1-hydroxyeth-1-yl)-4-nitrophenyl)oxyheptanamide;
N-cyclohexyl-N-acetoxypropyl-6-(3-(1-hydroxyeth-1-yl)-4-nitrophenyl)oxyhexanamide;
N-cyclohexyl-N-(2-acetoxyethyl)-4-(3-(1-hydroxyeth-1-yl)-4-nitrophenyl)oxybutanamide;
N-cyclohexyl-N-(2-acetoxyethyl)-4-(2-chloro-3-(1-hydroxyeth-1-yl)-4-nitrophenyl)oxybutanamide;

N-cyclohexylmethyl-N-(2-acetoxyethyl)-4-(3-(1-hydroxyeth-1-yl)-4-nitro-5-chlorophenyl)oxybutanamide;

N-hexyl-N-(2-acetoxyethyl)-4-(2-(1-hydroxyeth-1-yl)-3-nitro-6-fluorophenyl)oxybutanamide;

N-cyclohexyl-N-(6-acetoxyhexyl)-4-(2-(1-hydroxyeth-1-yl)-3-nitrophenyl)oxybutanamide;

N-cyclopentyl-N-(2-acetoxyethyl)-4-(3-nitro-4-(1-hydroxyeth-1-yl)-5-methylphenyl)oxybutanamide;

N-cyclopentylmethyl-N-(2-acetoxyethyl)-4-(2-nitro-3-(1-hydroxyeth-1-yl)-6-fluorophenyl)oxybutanamide;

N-cyclopentylbutyl-N-(2-acetoxyethyl)-4-(2-nitro-3-(1-hydroxyeth-1-yl)-6-chlorophenyl)oxybutanamide;

N-cyclohexyl-N-(2-acetoxyethyl)-5-(2-(1-hydroxyeth-1-yl)-3-nitro-6-methylphenyl)oxypentanamide;

N-cyclohexyl-N-(4-acetoxy-n-butyl)-7-(2-chloro-3-(1-hydroxyeth-1-yl)-4-nitrophenyl)oxyheptanamide;

N-cyclohexyl-N-(2-acetoxyethyl)-5-(2-nitro-3-(1-hydroxyeth-1-yl)-4-methylphenyl)oxypentanamide;

N-cyclohexyl-N-(2-acetoxyethyl)-6-(2-nitro-3-(1-hydroxyeth-1-yl)phenyl)oxyhexanamide; and N-cyclohexyl-N-(2-acetoxyethyl)-2-(3-(1-hydroxyeth-1-yl)-4-nitro-5-chlorophenyl)oxyacetamide.

PREPARATION 9

N-cyclohexyl-N-(2-acetoxyethyl)-4-(4-nitro-3-(1-oxoeth-1-yl)phenyl)oxybutanamide and related compounds of Formula 8

Oxidation of the alcohols of preparation 8 proceeds as previously described in preparation 6. Thus, proceeding from N-cyclohexyl-N-(2-acetoxyethyl)-4-(4-nitro-3-(1-oxoeth-1-yl)phenyl)oxybutanamide, oxidation with Collins reagent affords N-cyclohexyl-N-(2-acetoxyethyl)-4-(4-nitro-3-(ethan-1-on)phenyl)oxybutanamide. Similarly prepared from the corresponding alcohol of Preparation 8 are:

N-cyclohexyl-N-acetoxymethyl-4-(3-(1-oxoeth-1-yl)-4-nitrophenyl)oxybutanamide;

N-cyclohexyl-N-acetoxyethyl-4-(3-nitro-4-(1-oxoeth-1-yl)phenyl)oxybutanamide;

N-cyclohexyl-N-acetoxymethyl-4-(2-(1-oxoeth-1-yl)-3-nitrophenyl)oxybutanamide;

N-cyclohexyl-N-acetoxymethyl-4-(2-nitro-3-(1-oxoeth-1-yl)phenyl)oxybutanamide;

N-benzyl-N-(5-acetoxypentyl)-4-(3-(1-oxoeth-1-yl)-4-nitrophenyl)oxybutanamide;

N-cyclohexyl-N-acetoxymethyl-7-(3-(1-oxoeth-1-yl)-4-nitrophenyl)oxyheptanamide;

N-cyclohexyl-N-acetoxymethyl-6-(3-(1-oxoeth-1-yl)-4-nitrophenyl)oxyhexanamide;

N-cyclohexyl-N-(2-acetoxyethyl)-4-(3-(1-oxoeth-1-yl)-4-nitrophenyl)oxybutanamide;

N-cyclohexyl-N-(2-acetoxyethyl)-4-(2-chloro-3-(1-oxoeth-1-yl)-4-nitrophenyl)oxybutanamide;

N-cyclohexylmethyl-N-(2-acetoxyethyl)-4-(3-(1-oxoeth-1-yl)-4-nitro-5-chlorophenyl)oxybutanamide;

N-hexyl-N-(2-acetoxyethyl)-4-(2-(1-oxoeth-1-yl)-3-nitro-6-fluorophenyl)oxybutanamide;

N-cyclohexyl-N-(6-acetoxyhexyl)-4-(2-(1-oxoeth-1-yl)-3-nitrophenyl)oxybutanamide;

N-cyclopentyl-N-(2-acetoxyethyl)-4-(3-nitro-4-(1-oxoeth-1-yl)-5-methylphenyl)oxybutanamide;

N-cyclopentylmethyl-N-(2-acetoxyethyl)-4-(2-nitro-3-(1-oxoeth-1-yl)-6-fluorophenyl)oxybutanamide;

N-cyclopentylbutyl-N-(2-acetoxyethyl)-4-(2-nitro-3-(1-oxoeth-1-yl)-6-chlorophenyl)oxybutanamide;

N-cyclohexyl-N-(2-acetoxyethyl)-5-(2-(1-oxoeth-1-yl)-3-nitro-6-methylphenyl)oxypentanamide;

N-cyclohexyl-N-(4-acetoxy-n-butyl)-7-(2-chloro-3-(1-oxoeth-1-yl)-4-nitrophenyl)oxyheptanamide;

N-cyclohexyl-N-(2-acetoxyethyl)-5-(2-nitro-3-(1-oxoeth-1-yl)-4-methylphenyl)oxypentanamide;

N-cyclohexyl-N-(2-acetoxyethyl)-6-(2-nitro-3-(1-oxoeth-1-yl)phenyl)oxyhexanamide; and N-cyclohexyl-N-(2-acetoxyethyl)-2-(3-(1-oxoeth-1-yl)-4-nitro-5-chlorophenyl)oxyacetamide.

EXAMPLE 1

N-cyclohexyl-N-methyl-4-(2-oxo-3-hydroxymethyl-1,2,3,5-tetrahydroimidazo[2,1-b]quinazolin-7-yl)oxybutanamide To a solution of N-cyclohexyl-N-methyl-4-(3-formyl-4-nitrophenyl)oxybutanamide (25 mmol), D-serine methyl ester hydrochloride (7.0 g, 50 mmol) and 3 Å molecular sieves (5.0 g) in methanol (75 ml) was added D-serine methyl ester (20.6 g, 200 mmol). After allowing the solution to stir for 5 minutes at room temperature, sodium cyanoborohydride (0.95 g, 15 mmol) was added in one amount. The reaction mixture was allowed to stir at room temperature for 3-4 hours. The reaction solution was then filtered to remove precipitated solids and molecular sieves, and the methanol was removed by evaporation. The residue was dissolved in ethyl acetate (300 ml) and was washed with 2N sodium hydroxide (2×100 ml) in brine (2×100 ml). The organic extract was dried, filtered and evaporated to give a thick syrup. The thick syrupy residue was dissolved in absolute ethanol (100 ml) and hydrogenated over 10% Pd-C (1.0 g) until uptake of hydrogen ceased, approximately 4 hours. The catalyst was removed by filtration through a pad of Celite, and pad was washed clean with absolute ethanol (50 ml). The combined filtrates from the previous paragraph were treated with cyanogen bromide (3.20 g, 30 mmol), and the resulting solution maintained at room temperature for 16 hours, then treated with 10 ml of ammonium hydroxide (5 ml, 30 mmol) and stirred for 2 hours at room temperature. The product precipitated from this mixture and it was further purified by filtration and a water wash and dried, yielding N-cyclohexyl-N-methyl-4-(2-oxo-3-D-hydroxymethyl-1,2,3,5-tetrahydroimidazo[2,1-b]quinazolin-7-yl)oxybutanamide, m.p. 218°-219° C.

Proceeding in a like manner but substituting the appropriate aldehyde of formula (6) as prepared in Preparation 4, or the appropriate ketone of formula (8) as prepared in either Preparation 6 or 9, and either L-serine methyl ester or a racemic mixture of D,L-serine methyl ester or similar ester, there are prepared the following exemplary compounds:

N-cyclohexyl-N-methyl-4-(2-oxo-3-L-hydroxymethyl-1,2,3,5-tetrahydroimidazo[2,1-b]quinazolin-7-yl)oxybutanamide, m.p. 219°-220° C.;

N-cyclohexyl-N-methyl-4-(2-oxo-3-hydroxymethyl-1,2,3,5-tetrahydroimidazo[2,1-b]quinazolin-7-yl)oxybutanamide;

N-cyclohexyl-N-ethyl-4-(2-oxo-3-hydroxymethyl-1,2,3,5-tetrahydroimidazo[2,1-b]quinazolin-8-yl)oxybutanamide;

N-cyclohexyl-N-methyl-4-(2-oxo-3-hydroxymethyl-1,2,3,5-tetrahydroimidazo[2,1-b]quinazolin-6-yl)oxybutanamide;

N-cyclohexyl-N-methyl-4-(2-oxo-3-hydroxymethyl-1,2,3,5-tetrahydroimidazo[2,1-b]quinazolin-9-yl)oxybutanamide;

N-benzyl-N-pentyl-4-(2-oxo-3-hydroxymethyl-1,2,3,5-tetrahydroimidazo[2,1-b]quinazolin-7-yl)oxybutanamide;

N-cyclohexyl-N-methyl-7-(2-oxo-3-hydroxymethyl-1,2,3,5-tetrahydroimidazo[2,1-b]quinazolin-7-yl)oxyheptanamide;

N-cyclohexyl-N-methyl-6-(2-oxo-3-hydroxymethyl-1,2,3,5-tetrahydroimidazo[2,1-b]quinazolin-7-yl)oxyhexanamide;

N-morpholinyl-5-(2-oxo-3-hydroxymethyl-1,2,3,5-tetrahydroimidazo[2,1-b]quinazolin-7-yl)oxypentanamide;

N-cyclohexyl-N-hydroxyethyl-4-(2-oxo-3-hydroxymethyl-1,2,3,5-tetrahydroimidazo[2,1-b]quinazolin-7-yl)oxybutanamide;

N-cyclohexyl-N-hydroxyethyl-4-(2-oxo-3-hydroxymethyl-6-chloro-1,2,3,5-tetrahydroimidazo[2,1-b]quinazolin-7-yl)oxybutanamide;

N-cyclohexylmethyl-N-hydroxyethyl-4-(2-ox-3-hydroxymethyl-6-chloro-1,2,3,5-tetrahydroimidazo[2,1-b]quinazolin-7-yl)oxybutanamide;

N-hexyl-N-methyl-4-(2-oxo-3-hydroxymethyl-8-chloro-1,2,3,5-tetrahydroimidazo[2,1-b]quinazolin-7-yl)oxybutanamide;

N,N-dimethyl-4-(2-oxo-3-hydroxymethyl-9-fluoro-1,2,3,5-tetrahydroimidazo[2,1-b]quinazolin-7-yl)oxybutanamide;

N-ethyl-N-methyl-4-(2-oxo-3-hydroxymethyl-6-fluoro-1,2,3,5-tetrahydroimidazo[2,1-b]quinazolin-7-yl)oxyoxybutanamide;

N-pentyl-N-methyl-4-(2-oxo-3-hydroxymethyl-6-methyl-1,2,3,5-tetrahydroimidazo[2,1-b]quinazolin-7-yl)oxyoxybutanamide;

N-hexyl-N-hydroxyethyl-4-(2-oxo-3-hydroxymethyl-7-fluoro-1,2,3,5-tetrahydroimidazo[2,1-b]quinazolin-6-yl)oxybutanamide;

N,N-dihexyl-4-(2-oxo-3-hydroxymethyl-9-chloro-1,2,3,5-tetrahydroimidazo[2,1-b]quinazolin-6-yl)oxybutanamide;

N,N-dipentyl-4-(2-oxo-3-hydroxymethyl-8-fluoro-1,2,3,5-tetrahydroimidazo[2,1-b]quinazolin-6-yl)oxybutanamide;

N-cyclohexyl-N-6-hydroxyhexyl-4-(2-oxo-3-hydroxymethyl-1,2,3,5-tetrahydroimidazo[2,1-b]quinazolin-6-yl)oxybutanamide;

N-cyclohexyl-N-n-hexyl-4-(2-oxo-3-hydroxymethyl-8-methyl-1,2,3,5-tetrahydroimidazo[2,1-b]quinazolin-6-yl)oxybutanamide;

N-cyclopentyl-N-methyl-4-(2-oxo-3-hydroxymethyl-7-fluoro-1,2,3,5-tetrahydroimidazo[2,1-b]quinazolin-6-yl)oxybutanamide;

N-cyclopropylmethyl-N-methyl-4-(2-oxo-3-hydroxymethyl-1,2,3,5-tetrahydroimidazo[2,1-b]quinazolin-9-yl)oxybutanamide;

N-cycloheptyl-N-methyl-4-(2-oxo-3-hydroxymethyl-7-methyl-1,2,3,5-tetrahydroimidazo[2,1-b]quinazolin-9-yl)oxybutanamide;

N-cyclopentylbutyl-N-methyl-4-(2-oxo-3-hydroxymethyl-7-fluoro-1,2,3,5-tetrahydroimidazo[2,1-b]quinazolin-8-yl)oxybutanamide;

N-cyclopentylmethyl-N-methyl-4-(2-oxo-3-hydroxymethyl-8-chloro-1,2,3,5-tetrahydroimidazo[2,1-b]quinazolin-7-yl)oxybutanamide;

N-cyclopentyl-N-butyl-4-(2-oxo-3-hydroxymethyl-1,2,3,5-tetrahydroimidazo[2,1-b]quinazolin-8-yl)oxybutanamide;

N-cyclopentyl-N-hydroxyethyl-4-(2-oxo-3-hydroxymethyl-6-methyl-1,2,3,5-tetrahydroimidazo[2,1-b]quinazolin-8-yl)oxybutanamide;

N-cyclopentylmethyl-N-hydroxyethyl-4-(B 2-oxo-3-hydroxymethyl-8-methyl-1,2,3,5-tetrahydroimidazo[2,1-b]quinazolin-9-yl)oxybutanamide;

N-cyclopentylbutyl-N-hydroxyethyl-4-(2-oxo-3-hydroxymethyl-8-chloro-1,2,3,5-tetrahydroimidazo[2,1-b]quinazolin-9-yl)oxybutanamide;

N,N-dicyclohexyl-4-(2-oxo-3-hydroxymethyl-1,2,3,5-tetrahydroimidazo[2,1-b]quinazolin-7-yl)oxybutanamide;

N-cyclohexyl-N-4-hydroxy-n-butyl-7-(2-oxo-3-hydroxymethyl-6-chloro-1,2,3,5-tetrahydroimidazo[2,1-b]quinazolin-7-yl)oxyheptanamide;

N-phenyl-N-methyl-7-(2-oxo-3-hydroxymethyl-6-methyl-1,2,3,5-tetrahydroimidazo[2,1-b]quinazolin-7-yl)oxyheptanamide;

N-phenyl-N-methyl-4-(2-oxo-3-hydroxymethyl-1,2,3,5-tetrahydroimidazo[2,1-b]quinazolin-7-yl)oxybutanamide;

N-phenyl-N-hexyl-7-(2-oxo-3-hydroxymethyl-9-chloro-1,2,3,5-tetrahydroimidazo[2,1-b]-quinazolin-7-yl)oxyheptanamide;

N-phenyl-N-6-hydroxyhexyl-7-(2-oxo-3-hydroxymethyl-6-methyl-1,2,3,5-tetrahydroimidazo[2,1-b]quinazolin-6-yl)oxyheptanamide;

N-cyclohexyl-N-n-butyl-7-(2-oxo-3-hydroxymethyl-9-fluoro-1,2,3,5-tetrahydroimidazo[2,1-b]quinazolin-6-yl)oxyheptanamide;

N-benzyl-N-methyl-7-(2-oxo-3-hydroxymethyl-6-methyl-1,2,3,5-tetrahydroimidazo[2,1-b]quinazolin-7-yl)oxyheptanamide;

N-benzyl-N-methyl-4-(2-oxo-3-hydroxymethyl-6-methyl-1,2,3,5-tetrahydroimidazo[2,1-b]quinazolin-7-yl)oxybutanamide;

N,N-dibenzyl-7-(2-oxo-3-hydroxymethyl-8-chloro-1,2,3,5-tetrahydroimidazo[2,1-b]quinazolin-6-yl)oxyheptanamide;

N,N-dibenzyl-4-(2-oxo-3-hydroxymethyl-1,2,3,5-tetrahydroimidazo[2,1-b]quinazolin-7-yl)oxybutanamide;

N-diphenylmethyl-N-methyl-7-(2-oxo-3-hydroxymethyl-1,2,3,5-tetrahydroimidazo[2,1-b]quinazolin-9-yl)oxyheptanamide;

N-diphenylmethyl-N-methyl-4-(2-oxo-3-hydroxymethyl-1,2,3,5-tetrahydroimidazo[2,1-b]quinazolin-7-yl)oxybutanamide;

morpholinyl-4-(2-oxo-3-hydroxymethyl-1,2,3,5-tetrahydroimidazo[2,1-b]quinazolin-7-yl)oxybutanamide;

morpholinyl-7-(2-oxo-3-hydroxymethyl-6-fluoro-1,2,3,5-tetrahydroimidazo[2,1-b]quinazolin-9-yl)oxyheptanamide;

piperidinyl-7-(2-oxo-3-hydroxymethyl-8-chloro-1,2,3,5-tetrahydroimidazo[2,1-b]quinazolin-9-yl)oxyheptanamide;

piperidinyl-4-(2-oxo-3-hydroxymethyl-1,2,3,5-tetrahydroimidazo[2,1-b]quinazolin-7-yl)oxybutanamide;

pyrrolidinyl-7-(2-oxo-3-hydroxymethyl-7-methyl-1,2,3,5-tetrahydroimidazo[2,1-b]quinazolin-9-yl)oxyheptanamide;

pyrrolidinyl-4-(2-oxo-3-hydroxymethyl-1,2,3,5-tetrahydroimidazo[2,1-b]quinazolin-7-yl)oxybutanamide;

N-methylpiperazinyl-7-(2-oxo-3-hydroxymethyl-1,2,3,5-tetrahydroimidazo[2,1-b]quinazolin-7-yl)oxyheptanamide;

tetrahydroquinolinyl-7-(2-oxo-3-hydroxymethyl-6-methyl-1,2,3,5-tetrahydroimidazo[2,1-b]quinazolin-8-yl)oxyheptanamide;

tetrahydroquinolinyl-4-(2-oxo-3-hydroxymethyl-1,2,3,5-tetrahydroimidazo[2,1-b]quinazolin-7-yl)oxybutanamide;

tetrahydroisoquinolinyl-7-(2-oxo-3-hydroxymethyl-1,2,3,5-tetrahydroimidazo[2,1-b]quinazolin-6-yl)oxyheptanamide;

tetrahydroisoquinolinyl-4-(2-oxo-3-hydroxymethyl-1,2,3,5-tetrahydroimidazo[2,1-b]quinazolin-7-yl)oxybutanamide;

indolinyl-5-(2-oxo-3-hydroxymethyl-6-chloro-1,2,3,5-tetrahydroimidazo[2,1-b]quinazolin-9-yl)oxypentanamide;

indolinyl-4-(2-oxo-3-hydroxymethyl-1,2,3,5-tetrahydroimidazo[2,1-b]quinazolin-7-yl)oxybutanamide;

(±)-decahydroquinolinyl-5-(2-oxo-3-hydroxymethyl-9-methyl-1,2,3,5-tetrahydroimidazo[2,1-b]quinazolin-6-yl)oxypentanamide;

N-cyclohexyl-N-hydroxyethyl-5-(2-oxo-3-hydroxymethyl-7-methyl-1,2,3,5-tetrahydroimidazo[2,1-b]quinazolin-6-yl)oxypentanamide;

N-cyclohexyl-N-methyl-5-(2-oxo-3-hydroxymethyl-9-chloro-1,2,3,5-tetrahydroimidazo[2,1-b]quinazolin-7-yl)oxypentanamide;

N-cyclohexyl-N-4-hydroxy-n-butyl-5-(2-oxo-3-hydroxymethyl-6-chloro-1,2,3,5-tetrahydroimidazo[2,1-b]quinazolin-7-yl)oxypentanamide;

N-cyclohexyl-N-n-hexyl-5-(2-oxo-3-hydroxymethyl-1,2,3,5-tetrahydroimidazo[2,1-b]quinazolin-7-yl)oxypentanamide;

N-phenyl-N-methyl-5-(2-oxo-3-hydroxymethyl-1,2,3,5-tetrahydroimidazo[2,1-b]quinazolin-7-yl)oxypentanamide;

N-benzyl-N-methyl-5-(2-oxo-3-hydroxymethyl-9-methyl-1,2,3,5-tetrahydroimidazo[2,1-b]-quinazolin-7-yl)oxypentanamide;

N,N-dibenzyl-5-(2-oxo-3-hydroxymethyl-8-chloro-1,2,3,5-tetrahydroimidazo[2,1-b]-quinazolin-7-yl)oxypentanamide;

N,N-dicyclohexyl-5-(2-oxo-3-hydroxymethyl-8-chloro-1,2,3,5-tetrahydroimidazo[2,1-b]-quinazolin-7-yl)oxypentanamide;

(±)-decahydroquinolinyl-5-(2-oxo-3-hydroxymethyl-1,2,3,5-tetrahydroimidazo[2,1-b]quinazolin-9-yl)oxypentanamide;

N-cyclohexyl-N-hydroxyethyl-5-(2-oxo-3-hydroxymethyl-6-methyl-1,2,3,5-tetrahydroimidazo[2,1-b]quinazolin-9-yl)oxypentanamide;

N-phenyl-N-methyl-5-(2-oxo-3-hydroxymethyl-8-chloro-1,2,3,5-tetrahydroimidazo[2,1-b]quinazolin-9-yl)oxypentanamide;

N-cyclohexyl-N-methyl-6-(2-oxo-3-hydroxymethyl-1,2,3,5-tetrahydroimidazo[2,1-b]quinazolin-9-yl)oxyhexanamide;

N-benzyl-N-methyl-6-(2-oxo-3-hydroxymethyl-9-chloro-1,2,3,5-tetrahydroimidazo[2,1-b]quinazolin-6-yl)oxyhexanamide;

N,N-dibenzyl-6-(2-oxo-3-hydroxymethyl-7-chloro-1,2,3,5-tetrahydroimidazo[2,1-b]quinazolin-6-yl)oxyhexanamide;

N,N-dicyclohexyl-6-(2-oxo-3-hydroxymethyl-1,2,3,5-tetrahydroimidazo[2,1-b]quinazolin-7-yl)oxyhexanamide;

(±)-decahydroquinolinyl-6-(2-oxo-3-hydroxymethyl-8-chloro-1,2,3,5-tetrahydroimidazo[2,1-b]quinazolin-7-yl)oxyhexanamide;

N-diphenylmethyl-N-methyl-6-(2-oxo-3-hydroxymethyl-9-methyl-1,2,3,5-tetrahydroimidazo[2,1-b]quinazolin-7-yl)oxyhexanamide;

N-cyclohexyl-N-hydroxyethyl-6-(2-oxo-3-hydroxymethyl-1,2,3,5-tetrahydroimidazo[2,1-b]quinazolin-9-yl)oxyhexanamide;

N-cyclohexyl-N-methyl-6-(2-oxo-3-hydroxymethyl-8-fluoro-1,2,3,5-tetrahydroimidazo[2,1-b]quinazolin-9-yl)oxyhexanamide;

N-phenyl-N-methyl-6-(2-oxo-3-hydroxymethyl-7-methyl-1,2,3,5-tetrahydroimidazo[2,1-b]quinazolin-9-yl)oxyhexanamide;

N-benzyl-N-methyl-6-(2-oxo-3-hydroxymethyl-1,2,3,5-tetrahydroimidazo[2,1-b]quinazolin-8-yl)oxyhexanamide;

N,N-dibenzyl-6-(2-oxo-3-hydroxymethyl-7-methyl-1,2,3,5-tetrahydroimidazo[2,1-b]quinazolin-8-yl)oxyhexanamide;

N,N-dicyclohexyl-6-(2-oxo-3-hydroxymethyl-6-chloro-1,2,3,5-tetrahydroimidazo[2,1-b]quinazolin-8-yl)oxyhexanamide;

(±)-decahydroquinolinyl-2-(2-oxo-3-hydroxymethyl-6-chloro-1,2,3,5-tetrahydroimidazo[2,1-b]quinazolin-7-yl)oxyacetamide;

N-diphenylmethyl-N-methyl-2-(2-oxo-3-hydroxymethyl-1,2,3,5-tetrahydroimidazo[2,1-b]quinazolin-7-yl)oxyacetamide;

N-cyclohexyl-N-hydroxyethyl-2-(2-oxo-3-hydroxymethyl-9-chloro-1,2,3,5-tetrahydroimidazo[2,1-b]quinazolin-7-yl)oxyacetamide;

N-cyclohexyl-N-n-hexyl-2-(2-oxo-3-hydroxymethyl-8-chloro-1,2,3,5-tetrahydroimidazo[2,1-b]quinazolin-7-yl)oxyacetamide; and N-benzyl-N-methyl-2-(2-oxo-3-hydroxymethyl-9-fluoro-1,2,3,5-tetrahydroimidazo[2,1-b]quinazolin-7-yl)oxyacetamide.

EXAMPLE 2

N-cyclohexyl-N-methyl-4-(2-oxo-3-methylene-1,2,3,5-tetrahydroimidazo[2,1-b]quinazolin-7-yl)oxybutanamide To 500 ml of pyridine was added 5.14 g of N-cyclohexyl-N-methyl-4-(2-oxo-3-hydroxymethyl-1,2,3,5-tetrahydroimidazo[2,1-b]quinazolin-7-yl)oxybutanamide to which was added 0.9 ml of mesyl chloride. This solution was cooled to about 0°–5° C., at which time 7.12 ml of DIPEA was added. This solution was stirred at room temperature for 3 hours. The pyridine was stripped under high vacuum at about 40° C. to give a suspension which was trituratured with water, centrifuged and crystals of the captioned compound collected by filtration: m.p. 176°–178° C.

Proceeding in a similar manner, but substituting for N-cyclohexyl-N-methyl-4-(2-oxo-3-hydroxymethyl-1,2,3,5-tetrahydroimidazo[2,1-b]quinazolin-7-yl)oxybutanamide, any of the compounds made as per Example 1 there are prepared, for example, the following compounds:

N-cyclohexyl-N-methyl-4-(2-oxo-3-L-methylene-1,2,3,5-tetrahydroimidazo[2,1-b]quinazolin-7-yl)oxybutanamide;
N-cyclohexyl-N-methyl-4-(2-oxo-3-methylene-1,2,3,5-tetrahydroimidazo[2,1-b]quinazolin-7-yl)oxybutanamide;
N-cyclohexyl-N-ethyl-4-(2-oxo-3-methylene-1,2,3,5-tetrahydroimidazo[2,1-b]quinazolin-8-yl)oxybutanamide;
N-cyclohexyl-N-methyl-4-(2-oxo-3-methylene-1,2,3,5-tetrahydroimidazo[2,1-b]quinazolin-6-yl)oxybutanamide;
N-cyclohexyl-N-methyl-4-(2-oxo-3-methylene-1,2,3,5-tetrahydroimidazo[2,1-b]quinazolin-9-yl)oxybutanamide;
N-benzyl-N-pentyl-4-(2-oxo-3-methylene-1,2,3,5-tetrahydroimidazo[2,1-b]quinazolin-7-yl)oxybutanamide;
N-cyclohexyl-N-methyl-7-(2-oxo-3-methylene-1,2,3,5-tetrahydroimidazo[2,1-b]quinazolin-7-yl)oxyheptanamide;
N-cyclohexyl-N-methyl-6-(2-oxo-3-methylene-1,2,3,5-tetrahydroimidazo[2,1-b]quinazolin-7-yl)oxyhexanamide;
N-morpholinyl-5-(2-oxo-3-methylene-1,2,3,5-tetrahydroimidazo[2,1-b]quinazolin-7-yl)oxypentanamide;
N-cyclohexyl-N-hydroxyethyl-4-(2-oxo-3-methylene-1,2,3,5-tetrahydroimidazo[2,1-b]quinazolin-7-yl)oxybutanamide;
N-cyclohexyl-N-hydroxyethyl-4-(2-oxo-3-methylene-6-chloro-1,2,3,5-tetrahydroimidazo[2,1-b]quinazolin-7-yl)oxybutanamide;
N-cyclohexylmethyl-N-hydroxyethyl-4-(2-oxo-3-methylene-6-chloro-1,2,3,5-tetrahydroimidazo[2,1-b]quinazolin-7-yl)oxybutanamide;
N-hexyl-N-methyl-4-(2-oxo-3-methylene-8-chloro-1,2,3,5-tetrahydroimidazo[2,1-b]quinazolin-7-yl)oxybutanamide;
N,N-dimethyl-4-(2-oxo-3-methylene-9-fluoro-1,2,3,5-tetrahydroimidazo[2,1-b]quinazolin-7-yl)oxybutanamide;
N-ethyl-N-methyl-4-(2-oxo-3-methylene-6-fluoro-1,2,3,5-tetrahydroimidazo[2,1-b]quinazolin-7-yl)oxyoxybutanamide;
N-pentyl-N-methyl-4-(2-oxo-3-methylene-6-methyl-1,2,3,5-tetrahydroimidazo[2,1-b]quinazolin-7-yl)oxyoxybutanamide;
N-hexyl-N-hydroxyethyl-4-(2-oxo-3-methylene-7-fluoro-1,2,3,5-tetrahydroimidazo[2,1-b]quinazolin-6-yl)oxybutanamide;
N,N-dihexyl-4-(2-oxo-3-methylene-9-chloro-1,2,3,5-tetrahydroimidazo[2,1-b]quinazolin-6-yl)oxybutanamide;
N,N-dipentyl-4-(2-oxo-3-methylene-8-fluoro-1,2,3,5-tetrahydroimidazo[2,1-b]quinazolin-6-yl)oxybutanamide;
N-cyclohexyl-N-6-hydroxyhexyl-4-(2-oxo-3-methylene-1,2,3,5-tetrahydroimidazo[2,1-b]quinazolin-6-yl)oxybutanamide;
N-cyclohexyl-N-n-hexyl-4-(2-oxo-3-methylene-8-methyl-1,2,3,5-tetrahydroimidazo[2,1-b]quinazolin-6-yl)oxybutanamide;
N-cyclopentyl-N-methyl-4-(2-oxo-3-methylene-7-fluoro-1,2,3,5-tetrahydroimidazo[2,1-b]quinazolin-6-yl)oxybutanamide;
N-cyclopropylmethyl-N-methyl-4-(2-oxo-3-methylene-1,2,3,5-tetrahydroimidazo[2,1-b]quinazolin-9-yl)oxybutanamide;
N-cycloheptyl-N-methyl-4-(2-oxo-3-methylene-7-methyl-1,2,3,5-tetrahydroimidazo[2,1-b]quinazolin-9-yl)oxybutanamide;
N-cyclopentylbutyl-N-methyl-4-(2-oxo-3-methylene-7-fluoro-1,2,3,5-tetrahydroimidazo[2,1-b]quinazolin-8-yl)oxybutanamide;
N-cyclopentylmethyl-N-methyl-4-(2-oxo-3-methylene-8-chloro-1,2,3,5-tetrahydroimidazo[2,1-b]quinazolin-7-yl)oxybutanamide;
N-cyclopentyl-N-butyl-4-(2-oxo-3-methylene-1,2,3,5-tetrahydroimidazo[2,1-b]quinazolin-8-yl)oxybutanamide;
N-cyclopentyl-N-hydroxyethyl-4-(2-oxo-3-methylene-6-methyl-1,2,3,5-tetrahydroimidazo[2,1-b]quinazolin-8-yl)oxybutanamide;
N-cyclopentylmethyl-N-hydroxyethyl-4-(2-oxo-3-methylidenyl-8-methyl-1,2,3,5-tetrahydroimidazo[2,1-b]quinazolin-9-yl)oxybutanamide;
N-cyclopentylbutyl-N-hydroxyethyl-4-(2-oxo-3-methylene-8-chloro-1,2,3,5-tetrahydroimidazo[2,1-b]quinazolin-9-yl)oxybutanamide;
N,N-dicyclohexyl-4-(2-oxo-3-methylene-1,2,3,5-tetrahydroimidazo[2,1-b]quinazolin-7-yl)oxybutanamide;
N-cyclohexyl-N-4-hydroxy-n-butyl-7-(2-oxo-3-methylene-6-chloro-1,2,3,5-tetrahydroimidazo[2,1-b]quinazolin-7-yl)oxyheptanamide;
N-phenyl-N-methyl-7-(2-oxo-3-methylene-6-methyl-1,2,3,5-tetrahydroimidazo[2,1-b]quinazolin-7-yl)oxyheptanamide;
N-phenyl-N-methyl-4-(2-oxo-3-methylene-1,2,3,5-tetrahydroimidazo[2,1-b]quinazolin-7-yl)oxybutanamide;
N-phenyl-N-hexyl-7-(2-oxo-3-methylene-9-chloro-1,2,3,5-tetrahydroimidazo[2,1-b]-quinazolin-7-yl)oxyheptanamide;
N-phenyl-N-6-hydroxyhexyl-7-(2-oxo-3-methylene-6-methyl-1,2,3,5-tetrahydroimidazo[2,1-b]quinazolin-6-yl)oxyheptanamide;
N-cyclohexyl-N-n-butyl-7-(2-oxo-3-methylene-9-fluoro-1,2,3,5-tetrahydroimidazo[2,1-b]quinazolin-6-yl)oxyheptanamide;
N-benzyl-N-methyl-7-(2-oxo-3-methylene-6-methyl-1,2,3,5-tetrahydroimidazo[2,1-b]quinazolin-7-yl)oxyheptanamide;
N-benzyl-N-methyl-4-(2-oxo-3-methylene-6-methyl-1,2,3,5-tetrahydroimidazo[2,1-b]quinazolin-7-yl)oxybutanamide;
N,N-dibenzyl-7-(2-oxo-3-methylene-8-chloro-1,2,3,5-tetrahydroimidazo[2,1-b]quinazolin-6-yl)oxyheptanamide;
N,N-dibenzyl-4-(2-oxo-3-methylene-1,2,3,5-tetrahydroimidazo[2,1-b]quinazolin-7-yl)oxybutanamide;
N-diphenylmethyl-N-methyl-7-(2-oxo-3-methylene-1,2,3,5-tetrahydroimidazo[2,1-b]quinazolin-9-yl)oxyheptanamide;
N-diphenylmethyl-N-methyl-4-(2-oxo-3-methylene-1,2,3,5-tetrahydroimidazo[2,1-b]quinazolin-7-yl)oxybutanamide;
morpholinyl-4-(2-oxo-3-methylene-1,2,3,5-tetrahydroimidazo[2,1-b]quinazolin-7-yl)oxybutanamide;
morpholinyl-7-(2-oxo-3-methylene-6-fluoro-1,2,3,5-tetrahydroimidazo[2,1-b]quinazolin-9-yl)oxyheptanamide;

piperidinyl-7-(2-oxo-3-methylene-8-chloro-1,2,3,5-tetrahydroimidazo[2,1-b]quinazolin-9-yl)oxyheptanamide;

piperidinyl-4-(2-oxo-3-methylene-1,2,3,5-tetrahydroimidazo[2,1-b]quinazolin-7-yl)oxybutanamide;

pyrrolidinyl-7-(2-oxo-3-methylene-7-methyl-1,2,3,5-tetrahydroimidazo[2,1-b]quinazolin-9-yl)oxyheptanamide;

pyrrolidinyl-4-(2-oxo-3-methylene-1,2,3,5-tetrahydroimidazo[2,1-b]quinazolin-7-yl)oxybutanamide;

N-methylpiperazinyl-7-(2-oxo-3-methylene-1,2,3,5-tetrahydroimidazo[2,1-b]quinazolin-7-yl)oxyheptanamide;

tetrahydroquinolinyl-7-(2-oxo-3-methylene-6-methyl-1,2,3,5-tetrahydroimidazo[2,1-b]quinazolin-8-yl)oxyheptanamide;

tetrahydroquinolinyl-4-(2-oxo-3-methylene-1,2,3,5-tetrahydroimidazo[2,1-b]quinazolin-7-yl)oxybutanamide;

tetrahydroisoquinolinyl-7-(2-oxo-3-methylene-1,2,3,5-tetrahydroimidazo[2,1-b]quinazolin-6-yl)oxyheptanamide;

tetrahydroisoquinolinyl-4-(2-oxo-3-methylene-1,2,3,5-tetrahydroimidazo[2,1-b]quinazolin-7-yl)oxybutanamide;

indolinyl-5-(2-oxo-3-methylene-6-chloro-1,2,3,5-tetrahydroimidazo[2,1-b]quinazolin-9-yl)oxypentanamide;

indolinyl-4-(2-oxo-3-methylene-1,2,3,5-tetrahydroimidazo[2,1-b]quinazolin-7-yl)oxybutanamide;

(±)-decahydroquinolinyl-5-(2-oxo-3-methylene-9-methyl-1,2,3,5-tetrahydroimidazo[2,1-b]quinazolin-6-yl)oxypentanamide;

N-cyclohexyl-N-hydroxyethyl-5-(2-oxo-3-methylene-7-methyl-1,2,3,5-tetrahydroimidazo[2,1-b]quinazolin-6-yl)oxypentanamide;

N-cyclohexyl-N-methyl-5-(2-oxo-3-methylene-9-chloro-1,2,3,5-tetrahydroimidazo[2,1-b]quinazolin-7-yl)oxypentanamide;

N-cyclohexyl-N-4-hydroxy-n-butyl-5-(2-oxo-3-methylene-6-chloro-1,2,3,5-tetrahydroimidazo[2,1-b]quinazolin-7-yl)oxypentanamide;

N-cyclohexyl-N-n-hexyl-5-(2-oxo-3-methylene-1,2,3,5-tetrahydroimidazo[2,1-b]quinazolin-7-yl)oxypentanamide;

N-phenyl-N-methyl-5-(2-oxo-3-methylene-1,2,3,5-tetrahydroimidazo[2,1-b]quinazolin-7-yl)oxypentanamide;

N-benzyl-N-methyl-5-(2-oxo-3-methylene-9-methyl-1,2,3,5-tetrahydroimidazo[2,1-b]-quinazolin-7-yl)oxypentanamide;

N,N-dibenzyl-5-(2-oxo-3-methylene-8-chloro-1,2,3,5-tetrahydroimidazo[2,1-b]-quinazolin-7-yl)oxypentanamide;

N,N-dicyclohexyl-5-(2-oxo-3-methylene-8-chloro-1,2,3,5-tetrahydroimidazo[2,1-b]-quinazolin-7-yl)oxypentanamide;

(±)-decahydroquinolinyl-5-(2-oxo-3-methylene-1,2,3,5-tetrahydroimidazo[2,1-b]quinazolin-9-yl)oxypentanamide;

N-cyclohexyl-N-hydroxyethyl-5-(2-oxo-3-methylene-6-methyl-1,2,3,5-tetrahydroimidazo[2,1-b]quinazolin-9-yl)oxypentanamide;

N-phenyl-N-methyl-5-(2-oxo-3-methylene-8-chloro-1,2,3,5-tetrahydroimidazo[2,1-b]quinazolin-9-yl)oxypentanamide;

N-cyclohexyl-N-methyl-6-(2-oxo-3-methylene-1,2,3,5-tetrahydroimidazo[2,1-b]quinazolin-9-yl)oxyhexanamide;

N-benzyl-N-methyl-6-(2-oxo-3-methylene-9-chloro-1,2,3,5-tetrahydroimidazo[2,1-b]quinazolin-6-yl)oxyhexanamide;

N,N-dibenzyl-6-(2-oxo-3-methylene-7-chloro-1,2,3,5-tetrahydroimidazo[2,1-b]quinazolin-6-yl)oxyhexanamide;

N,N-dicyclohexyl-6-(2-oxo-3-methylene-1,2,3,5-tetrahydroimidazo[2,1-b]quinazolin-7-yl)oxyhexanamide;

(±)-decahydroquinolinyl-6-(2-oxo-3-methylene-8-chloro-1,2,3,5-tetrahydroimidazo[2,1-b]quinazolin-7-yl)oxyhexanamide;

N-diphenylmethyl-N-methyl-6-(2-oxo-3-methylene-9-methyl-1,2,3,5-tetrahydroimidazo[2,1-b]quinazolin-7-yl)oxyhexanamide;

N-cyclohexyl-N-hydroxyethyl-6-(2-oxo-3-methylene-1,2,3,5-tetrahydroimidazo[2,1-b]quinazolin-9-yl)oxyhexanamide;

N-cyclohexyl-N-methyl-6-(2-oxo-3-methylene-8-fluoro-1,2,3,5-tetrahydroimidazo[2,1-b]quinazolin-9-yl)oxyhexanamide;

N-phenyl-N-methyl-6-(2-oxo-3-methylene-7-methyl-1,2,3,5-tetrahydroimidazo[2,1-b]quinazolin-9-yl)oxyhexanamide;

N-benzyl-N-methyl-6-(2-oxo-3-methylene-1,2,3,5-tetrahydroimidazo[2,1-b]quinazolin-8-yl)oxyhexanamide;

N,N-dibenzyl-6-(2-oxo-3-methylene-7-methyl-1,2,3,5-tetrahydroimidazo[2,1-b]quinazolin-8-yl)oxyhexanamide;

N,N-dicyclohexyl-6-(2-oxo-3-methylene-6-chloro-1,2,3,5-tetrahydroimidazo[2,1-b]quinazolin-8-yl)oxyhexanamide;

(±)-decahydroquinolinyl-2-(2-oxo-3-methylene-6-chloro-1,2,3,5-tetrahydroimidazo[2,1-b]quinazolin-7-yl)oxyacetamide;

N-diphenylmethyl-N-methyl-2-(2-oxo-3-methylene-1,2,3,5-tetrahydroimidazo[2,1-b]quinazolin-7-yl)oxyacetamide;

N-cyclohexyl-N-hydroxyethyl-2-(2-oxo-3-methylene-9-chloro-1,2,3,5-tetrahydroimidazo[2,1-b]quinazolin-7-yl)oxyacetamide;

N-cyclohexyl-N-n-hexyl-2-(2-oxo-3-methylene-8-chloro-1,2,3,5-tetrahydroimidazo[2,1-b]quinazolin-7-yl)oxyacetamide; and N-benzyl-N-methyl-2-(2-oxo-3-methylene-9-fluoro-1,2,3,5-tetrahydroimidazo[2,1-b]quinazolin-7-yl)oxyacetamide.

EXAMPLE 3

N-cyclohexyl-N-(2-hydroxyethyl)-4-(2-oxo-3-methylene-1,2,3,5-tetrahydroimidazo[2,1-b]quinazolin-7-yl)oxybutanamide To a solution of N-cyclohexyl-N-(2-acetoxyethyl)-4-(2-oxo-3-methylene-1,2,3,5-tetrahydroimidazo[2,1-b]quinazolin-7-yl)oxybutanamide 50 mg in ethanol (20 ml) was added 3N NaOH (5 ml) in small portions. After 30 minutes at room temperature, the reaction mixture was neutralized with concentrated HCl and the resulting precipitate was collected by filtration and dried to give the title compound.

Following this procedure, all esters prepared herein may be hydrolyzed to give the N-hydroxyalkyl analogs.

EXAMPLE 4

Conversion of Free Base to Salt

A two-fold stoichiometric excess of 3% hydrogen chloride in methanol is added to a solution of 1.0 g. of N-cyclohexyl-N-methyl-4-(2-oxo-3-methylene-1,2,3,5-tetrahydroimidazo-[2,1-b]quinazolin-7-yl)oxybutanamide in 20 ml methanol. Diethyl ether is added until precipitation is complete. The product is filtered, washed with ether, air dried and recrystallized to give N-cyclohexyl-N-methyl-4-(2-oxo-3-methylene-1,2,3,5-tetrahydroimidazo[2,1-b]-quinazolin-7-yl)oxybutanamide hydrochloride.

In a similar manner, all compounds of formula I in free base form may be converted to the acid addition salt by treatment with hydrogen chloride or another pharmaceutically acceptable acid addition salt-forming acid such as exemplified herein earlier.

EXAMPLE 5

Conversion of Salt to Free Base 1.0 g of N-cyclohexyl-N-methyl-4-(2-oxo-3-methylene-1,2,3,5-tetrahydroimidazo[2,1-b]quinazolin-7-yl)oxybutanamide HCl suspended in 50 ml of ether is stirred with a twofold stoichiometric excess of dilute aqueous potassium carbonate solution until the salt is completely dissolved. The organic layer is then separated, washed twice with water, dried over magnesium sulfate and evaporated to yield N-cyclohexyl-N-methyl-4-(2-oxo-3-methylene-1,2,3,5-tetrahydroimidazo[2,1-b]quinazolin-7-yl)oxybutanamide as the free base.

EXAMPLE 6

Direct interchange of acid addition salts

N,N-dibenzyl-4-(2-oxo-3-methylene-1,2,3,5-tetrahydroimidazo[2,1-b]quinazolin-7-yl)oxybutanamide acetate (1.0 g) is dissolved in 50 ml water containing a stoichiometric equivalent of sulfuric acid, and the solution evaporated to dryness. The product is suspended in ethanol and filtered, air dried and recrystallized from methanol/acetone to yield N,N-dibenzyl-4-(2-oxo-1,2,3,5-tetrahydroimidazo[2,1-b]quinazolin-7-yl)oxybutanamide sulfate.

EXAMPLE 7

Compounds of the present invention, either the free base or a pharmaceutically acceptable acid addition salt, may be orally administered to a subject as a tablet. While the active ingredient may comprise anywhere between 5 and 90 percent of the formulation that percentage preferably will be an amount which will cause to be delivered to the subject, the active ingredient in an amount of between 20 mg and 100 mg per tablet. Following is a representative tablet formulation in which the active ingredient is N-cyclohexyl-N-methyl-4-(2-oxo-3-methylene-1,2,3,5-tetrahydroimidazo[2,1-b]quinazolin-7-yl)oxybutanamide. However, the formulation profile given below may be used to formulate a tablet for any of the compounds represented by Formula I.

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 8

An alternative oral dosage form is to fill hard shell gelatin capsules with a powder containing the active ingredient in the desired amount. Using the active ingredient mentioned in Example 6 above, the acid addition salts, or any other compound according to Formula I there may be prepared an exemplary hard shell gelatin capsule formulation using the following ingredients

| Ingredients | Quantity per tablet, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 9

Alternatively, compounds of the present invention may be prepared as a suspension for oral administration. Any of the compounds of formula I, either in free base form or as the acid addition salt, may be used in this formulation.

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE 10

Cyclic AMP phosphodiesterase activity and inhibition of platelet aggregation were determined as follows.

Cyclic AMP phosphodiesterase assay

The inhibition of cyclic AMP phosphodiesterase activity by the subject compounds was assayed by the method of Filburn and Karn, *Analyt. Biochem.*, 52: 505–516 (1973), using 1 $\mu$M cyclic AMP as the substrate. Human platelet cyclic AMP phosphodiesterase was obtained from human donors. Platelets were isolated and washed by centrifugation, the membranes ruptured by a sequential freeze-thaw procedure and hypotonic lysis and the soluble enzyme isolated by high speed centrifugation. The enzyme was stored in aliquots at $-20°$ C.

By this method, N-cyclohexyl-N-methyl-4-(2-oxo-3-methylene-1,2,3,5-tetrahydroimidazo-[2,1-b]quinazolin-7-yl)oxybutanamide exhibited an IC$_{50}$ value of $2.7 \times 10^{-9}$M.

Platelet Aggregation

Blood was collected into evacuated tubes containing sodium citrate (30 mM). Platelet rich plasma was collected after centrifugation. Aggregation was followed by a turbidimetric procedure described by G. V. R. Born, *J. Physiol., Lond.*, 162: 67P–68P (1962).

By this method, N-cyclohexyl-N-methyl-4-(2-oxo-3-methylene-1,2,3,5-tetrahydroimidazo-[2,1-b]quinazolin-7-yl)oxybutanamide exhibited an $IC_{50}$ value of $1.5 \times 10^{-7}$M.

EXAMPLE 11

Inotropic Activity of the Compounds of the Present Invention

The inotropic activity of these compounds was determined as follows: Mongrel dogs were anesthetized i.v. with 35 mg/Kg sodium pentobarbital and supplemented as needed. Blood pressure was measured with a Statham pressure transducer via a cannula inserted from a femoral artery into the abdominal aorta. Heart rate was recorded by a cardiotachometer from a lead II electrocardiogram. Right ventricular contractile force was recorded from a Walton-Brodie strain gauge sutured to the right ventricle following a midsternal thoracotomy. A Harvard respirator was used to ventilate the dogs with room air through an endotracheal tube. The dog was bilaterally vagotomized. Following a midline laparotomy, a cannula was sutured into the duodenum for intraduodenal administration of test compound. A femoral vein was cannulated for administration of isoproterenol. All data were recorded on a Beckman R611 Dynograph.

To assess the responsiveness of each dog, isoproterenol was given i.v. at half-log interval doses from 0.007 to 2.1 or 6.67 μg/Kg. The test compound, N-cyclohexyl-N-methyl-4-(2-oxo-3-methylene-1,2,3,5-tetrahydroimidazo-[2,1-b]quinazolin-7-yl)oxybutanamide, was then administered intravenously at dose levels from 0.1 to 1.0 mg/Kg.

The results are summarized in Table I below.

TABLE I

| Compound | Dose(mg/kg) | Peak Effects as % of Max. Isoproterenol | | |
| --- | --- | --- | --- | --- |
| | | Rt. Ventricular Contractile Force | Heart Rate | Blood Pressure |
| N—cyclohexyl-N—methyl- | 0.1 | 24 | 18 | 42 |
| (2-oxo-3-methylene- | 0.316 | 52 | 28 | 58 |
| 1,2,3,5-tetrahydro- | 1.0 | 62 | 34 | 65 |
| imidazo-[2,1-b]quinazolin- | | | | |
| 7-yl)oxybutanamide | | | | |

What is claimed is:

1. A compound according to the formula

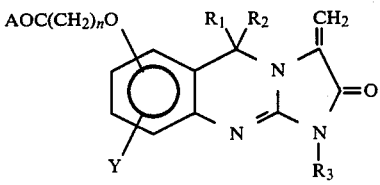

or an optical isomer thereof or a pharmaceutically acceptable acid addition salt thereof, wherein n is 1 or an integer of 3 to 6;

$R_1$ is hydrogen or alkyl of 1 to 4 carbon atoms;

$R_2$ is hydrogen or $R_1$ and $R_2$ are combined to form an oxo group;

$R_3$ is hydrogen, alkyl of 1 to 6 carbon atoms, benzyl, or hydroxy lower alkyl;

Y is hydrogen, alkyl of 1 to 4 carbon atoms, halo or lower alkoxy;

A is $NR_5R_6$ wherein $R_5$ an $R_6$ are independently selected from the group consisting of:
hydrogen; alkyl of 1 to 6 carbon atoms; hydroxyalkyl of 1 to 6 carbon atoms or an aliphatic acylate thereof of 1 to 6 carbon atoms or an aryl acylate thereof of 7 to 12 carbon atoms; cycloalkyl of 3 to 8 carbon atoms or cycloalkyl lower alkyl of 4 to 12 carbon atoms wherein the cycloalkyl ring is unsubstituted or substituted with a lower alkyl, lower alkoxy, —$OCOR_7$, halo, —$NH_2$, —$N(R_7)_2$, —$NHCOR_7$, or —$COO(R_7)$ group wherein $R_7$ is lower alkyl; phenyl or phenyl lower alkyl wherein phenyl is unsubstituted or substituted with at least one lower alkyl, halo or lower alkoxy group or an —$N(R_7)_2$, —NH-$COR_7$, or —$COOR_7$ group wherein $R_7$ is lower alkyl;

or wherein $R_5$, $R_6$ and the nitrogen of A are combined to form a radical selected from the group consisting of: morpholinyl; piperidinyl; perhexylenyl; N-loweralkylpiperazinyl; pyrrolidinyl; tetrahydroquinolinyl; tetrahydroisoquinolinyl; (±)-decahydroquinolinyl; and indolinyl.

2. A compound of claim 1 wherein $R_1$, $R_2$ and $R_3$ are each independently hydrogen or methyl and n is 3 or 4.

3. A compound of claim 1 wherein $R_1$ and $R_2$ are hydrogen and $R_3$ is hydrogen or methyl.

4. A compound according to claim 1 wherein the $R_5$ and $R_6$ substituents are selected from the group consisting of: alkyl of 1 to 6 carbon atoms; hydroxyalkyl of 2 to 6 carbon atoms or an aliphatic acylate thereof of 1 to 6 carbon atoms or an aryl acylate thereof of 7 to 12 carbon atoms; cycloalkyl of 3 to 8 carbon atoms; cycloalkyl lower alkyl of 4 to 12 carbon atoms; and phenyl or phenyl lower alkyl wherein the phenyl ring is unsubstituted or substituted with 1 or more lower alkyl, halo or lower alkoxy groups; or wherein the nitrogen, $R_5$ and $R_6$ together form a radical from the group consisting of perhexylenyl, (±)-decahydroquinolinyl, morpholinyl, piperidinyl, pyrrolidinyl, tetrahydroquinolinyl, tetrahydroisoquinolinyl and indolinyl.

5. A compound according to claim 2 wherein $R_4$ is hydrogen, n is 3 or 4 and $R_5$ and $R_6$ are selected from the group consisting of alkyl of 1 to 6 carbon atoms; hydroxyalkyl of 2 to 6 carbon atoms or an aliphatic acylate thereof of 1 to 6 carbon atoms or an aryl acylate thereof of 7 to 12 carbon atoms; cycloalkyl of 3 to 8 carbon atoms; and cycloalkyl lower alkyl of 4 to 12 carbon atoms.

6. A compound according to claim 3 wherein n is 3 and $R_5$ and $R_6$ are selected from the group consisting of alkyl of 1 to 6 carbon atoms and cycloalkyl of 3 to 8 carbon atoms.

7. A compound according to claim 4 selected from the group consisting of:

N-cyclohexyl-N-methyl-4-(2-oxo-3-methylene-1,2,3,5-tetrahydroimidazo-[2,1-b]quinazolin-7-yl)oxybutanamide;

N-cyclohexyl-N-cyclohexyl-4-(2-oxo-3-methylene-1,2,3,5-tetrahydro-imidazo[2,1-b]quinazolin-7-yl)oxybutanamide;

N-cyclohexyl-N-methyl-4-(2-oxo-3-methylene-1,2,3,5-tetrahydroimidazo-[2,1-b]quinazolin-9-yl)oxybutanamide;

N-cyclohexyl-N-methyl-4-(2-oxo-3-methylene-1,2,3,5-tetrahydroimidazo-[2,1-b]quinazolin-8-yl)oxybutanamide;

N-cyclohexyl-N-methyl-4-(2-oxo-3-methylene-1,2,3,5-tetrahydroimidazo-[2,1-b]quinazolin-6-yl)oxybutanamide;

N-cyclooctyl-N-methyl-4-(2-oxo-3-methylene-1,2,3,5-tetrahydroimidazo-[2,1-b]quinazolin-7-yl)oxybutanamide;

N-cyclopentyl-N-methyl-4-(2-oxo-3-methylene-1,2,3,5-tetrahydroimidazo-[2,1-b]quinazolin-7-yl)oxybutanamide;

N-cyclohexyl-N-ethyl-4-(2-oxo-3-methylene-1,2,3,5-tetrahydroimidazo-[2,1-b]quinazolin-7-yl)oxybutanamide;

N-cyclohexyl-N-isopropyl-4-(2-oxo-3-methylene-1,2,3,5-tetrahydro-imidazo[2,1-b]quinazolin-7-yl)oxybutanamide;

N-cyclohexyl-N-2-methoxyethyl-4-(2-oxo-3-methylene-1,2,3,5-tetrahydro-imidazo[2,1-b]quinazolin-7-yl)oxybutanamide;

N-cyclohexyl-N-n-butyl-4-(2-oxo-3-methylene-1,2,3,5-tetrahydro-imidazo[2,1-b]quinazolin-7-yl)oxybutanamide;

N-cycloheptyl-N-methyl-4-(2-oxo-3-methylene-1,2,3,5-tetrahydro-imidazo[2,1-b]quinazolin-7-yl)oxybutanamide; and pharmaceutically acceptable acid addition salts of each of the foregoing.

8. The compound according to claim 4, wherein $R_5$ and $R_6$ are respectively methyl and cyclohexyl and the oxybutanamide is substituted at position 7, namely, N-cyclohexyl-N-methyl-4-(2-oxo-3-methylene-1,2,3,5-tetrahydroimidazo-[2,1-b]quinazolin-7-yl)oxybutanamide, or a pharmaceutically acceptable acid addition salt thereof.

9. A method for treating heart failure, said method comprising administering a therapeutically effective amount of a compound of the formula

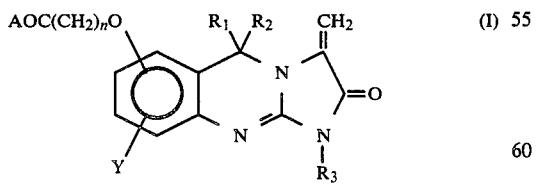

or an optical isomer thereof or a pharmaceutically acceptable acid addition salt thereof, wherein n is 1 or an integer of 3 to 6;

$R_1$ is hydrogen or alkyl of 1 to 4 carbon atoms;

$R_2$ is hydrogen or $R_1$ and $R_2$ are combined to form an oxo group;

$R_3$ is hydrogen, alkyl of 1 to 6 carbon atoms, benzyl, or hydroxy lower alkyl;

Y is hydrogen, alkyl of 1 to 4 carbon atoms, halo or lower alkoxy;

A is $NR_5R_6$ wherein $R_5$ an $R_6$ are independently selected from the group consisting of:

hydrogen; alkyl of 1 to 6 carbon atoms; hydroxyalkyl of 1 to 6 carbon atoms or an aliphatic acylate thereof of 1 to 6 carbon atoms or an aryl acylate thereof of 7 to 12 carbon atoms; cycloalkyl of 3 to 8 carbon atoms or cycloalkyl lower alkyl of 4 to 12 carbon atoms wherein the cycloalkyl ring is unsubstituted or substituted with a lower alkyl, lower alkoxy, —$OCOR_7$, halo, —$NH_2$, —$N(R_7)_2$, —$NHCOR_7$, or —$COO(R_7)$ group wherein $R_7$ is lower alkyl; phenyl or phenyl lower alkyl wherein phenyl is unsubstituted or substituted with at least one lower alkyl, halo or lower alkoxy group or an —$N(R_7)_2$, —$NHCOR_7$, or —$COOR_7$ group wherein $R_7$ is lower alkyl;

or wherein $R_5$, $R_6$ and the nitrogen of A are combined to form a radical selected from the group consisting of: morpholinyl; piperidinyl; perhexylenyl; N-loweralkylpiperazinyl; pyrrolidinyl; tetrahydroquinolinyl; tetrahydroisoquinolinyl; (±)-decahydroquinolinyl; and indolinyl;

to a subject in need thereof.

10. A method for inhibiting 3',5'-cyclic AMP phosphodiesterase activity in a mammal, said method comprising administering a therapeutically effective amount of a compound of the formula

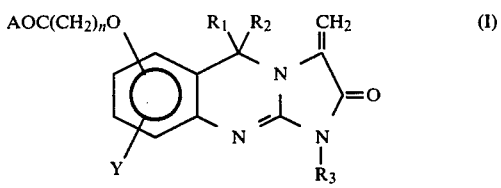

or an optical isomer thereof or a pharmaceutically acceptable acid addition salt thereof, wherein n is 1 or an integer of 3 to 6;

$R_1$ is hydrogen or alkyl of 1 to 4 carbon atoms;

$R_2$ is hydrogen or $R_1$ and $R_2$ are combined to form an oxo group;

$R_3$ is hydrogen, alkyl of 1 to 6 carbon atoms, benzyl, or hydroxy lower alkyl;

Y is hydrogen, alkyl of 1 to 4 carbon atoms, halo or lower alkoxy;

A is $NR_5R_6$ wherein $R_5$ an $R_6$ are independently selected from the group consisting of:

hydrogen; alkyl of 1 to 6 carbon atoms; hydroxyalkyl of 1 to 6 carbon atoms or an aliphatic acylate thereof of 1 to 6 carbon atoms or an aryl acylate thereof of 7 to 12 carbon atoms; cycloalkyl of 3 to 8 carbon atoms or cycloalkyl lower alkyl of 4 to 12 carbon atoms wherein the cycloalky ring is unsubstituted or substituted with a lower alkyl, lower alkoxy, —$OCOR_7$, halo, —$NH_2$, —$N(R_7)_2$, —$NHCOR_7$, or —$COO(R_7)$ group wherein $R_7$ is lower alkyl; phenyl or phenyl lower alkyl wherein phenyl is unsubstituted or substituted with at least one lower alkyl, halo or lower alkoxy group or an —$N(R_7)_2$, —NH- $COR_7$, or $—COOR_7$ group wherein $R_7$ is lower alkyl;

or wherein $R_5$, $R_6$ and the nitrogen of A are combined to form a radical selected from the group consisting of: morpholinyl; piperidinyl; perhexylenyl; N-loweralkylpiperazinyl; pyrrolidinyl; tetrahydroquinolinyl; tetahydroisoquinolinyl; (±)-decahydroquinolinyl; and indolinyl;

to a subject in need thereof.

* * * * *